United States Patent
Oku et al.

[11] Patent Number: 6,083,959
[45] Date of Patent: Jul. 4, 2000

[54] QUINOLINE DERIVATIVES, PROCESSES FOR THEIR PREPARATION AND THEIR USE AS MEDICAMENTS

[75] Inventors: Teruo Oku; Hiroshi Kayakiri; Shigeki Satoh; Yoshito Abe, all of Tsukuba; Yuki Sawada, Ushiku; Takayuki Inoue, Tsukuba; Hirokazu Tanaka, Takarazuka, all of Japan

[73] Assignee: Fujisawa Pharmaceutical Co., Ltd., Osaka, Japan

[21] Appl. No.: 09/147,193

[22] PCT Filed: Apr. 24, 1997

[86] PCT No.: PCT/JP97/01415

§ 371 Date: Oct. 26, 1998

§ 102(e) Date: Oct. 26, 1998

[87] PCT Pub. No.: WO97/15877

PCT Pub. Date: Apr. 24, 1997

[30] Foreign Application Priority Data

Apr. 29, 1996 [AU] Australia .................. PN9526

[51] Int. Cl.[7] .................. A61K 31/4709; C07D 401/04; C07D 401/14; A61P 29/00; A61P 37/08
[52] U.S. Cl. .................. 514/314; 514/241; 514/242; 514/254; 514/256; 514/235.2; 514/311; 544/128; 544/179; 544/182; 544/238; 544/333; 544/336; 546/167; 546/177
[58] Field of Search .................. 546/167, 177; 544/128, 179, 182, 238, 333, 336; 514/311, 314, 235.2, 241, 242, 254, 256

[56] References Cited

U.S. PATENT DOCUMENTS

| 5,212,182 | 5/1993 | Musser | 514/314 |
|---|---|---|---|
| 5,563,162 | 10/1996 | Oku et al. | 514/311 |
| 5,574,042 | 11/1996 | Oku et al. | 514/300 |
| 5,708,173 | 1/1998 | Oku et al. | 546/153 |
| 5,750,699 | 5/1998 | Oku et al. | 546/121 |

OTHER PUBLICATIONS

Stewart JM. Biopolymers (Peptide Science) 37, 143–155, 1955.
Stewart JM. Recent Progress on Kinins. Birkhauser Verlag Basel. pp. 546–550, 1992.

Primary Examiner—Evelyn Mei Huang
Attorney, Agent, or Firm—Oblon, Spivak, McClelland, Maier & Neustadt, P.C.

[57] ABSTRACT

A compound of the formula:

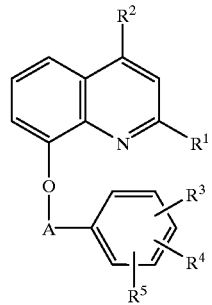

wherein
  $R^1$ is lower alkyl,
  $R^2$ is hydrogen, lower alkyl or a heterocyclic group,
  $R^3$ is hydrogen, lower alkyl or halogen,
  $R^4$ is lower alkyl or halogen,
  $R^5$ is nitro or amino substituted with substituent(s) selected from the group consisting of lower alkyl and acyl, and
  A is lower alkylene.

12 Claims, No Drawings

QUINOLINE DERIVATIVES, PROCESSES FOR THEIR PREPARATION AND THEIR USE AS MEDICAMENTS

This application is the national phase of PCT/JP97/01415, filed on Apr. 24, 1997.

TECHNICAL FIELD

This invention relates to new heterocyclic compounds and pharmaceutically acceptable salts thereof.

More particularly, it relates to new heterocyclic compounds and pharmaceutically acceptable salts thereof which have activities as bradykinin antagonists, to processes for preparation thereof, to a pharmaceutical composition comprising the same, and to methods of using the same therapeutically in the prevention and/or the treatment of bradykinin or its analogues mediated diseases such as allergy, inflammation, autoimmune disease, shock, pain, or the like, in human being or animals.

One object of this invention is to provide new and useful heterocyclic compounds and pharmaceutically acceptable salts thereof which possess activities as bradykinin antagonists.

Another object of this invention is to provide processes for the preparation of said compounds and salts thereof.

A further object of this invention is to provide a pharmaceutical composition comprising, as an active ingredient, said heterocyclic compounds and pharmaceutically acceptable salts thereof.

Still further object of this invention is to provide a therapeutical method for the prevention and/or the treatment of bradykinin or its analogues mediated diseases such as allergy, inflammation, autoimmune disease, shock, pain, or the like, using said heterocyclic compounds and pharmaceutically acceptable salts thereof.

BACKGROUND ART

Some heterocyclic compounds have been known as described, for example, in EP-A-224,086, EP-A-261,539, Chemical Abstracts 90:34849g (1979), or Chemical Abstracts 97:18948c (1982). However, it is not known that said compounds have activities as bradykinin antagonists.

Heterocyclic compounds having activities as bradykinin antagonists have been known as described in EP-A-596,406, EP-A-622,361, WO 96/13485 and WO 97/11069.

DISCLOSURE OF THE INVENTION

The object heterocyclic compounds of this invention are new and can be represented by the following general formula [I]:

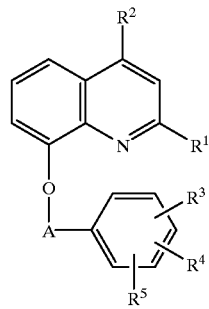

wherein $R^1$ is lower alkyl, $R^2$ is hydrogen, lower alkyl or a heterocyclic group, $R^3$ is hydrogen, lower alkyl or halogen, $R^4$ is lower alkyl or halogen, $R^5$ is nitro or amino substituted with substituent(s) selected from the group consisting of lower alkyl and acyl, and A is lower alkylene, provided that $R^3$ and $R^4$ are each lower alkyl when $R^2$ is hydrogen or lower alkyl.

The object compound [I] or its salt can be prepared by processes as illustrated in the following reaction schemes.

Process 1

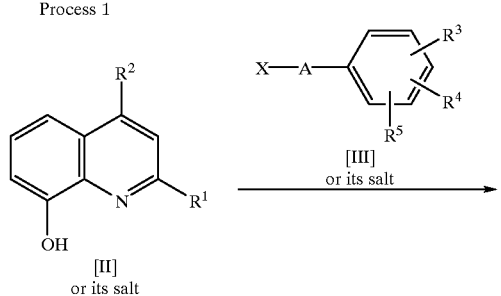

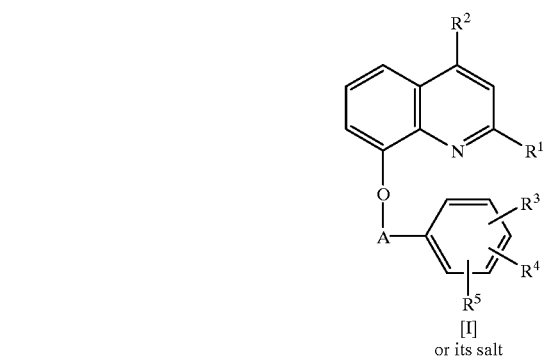

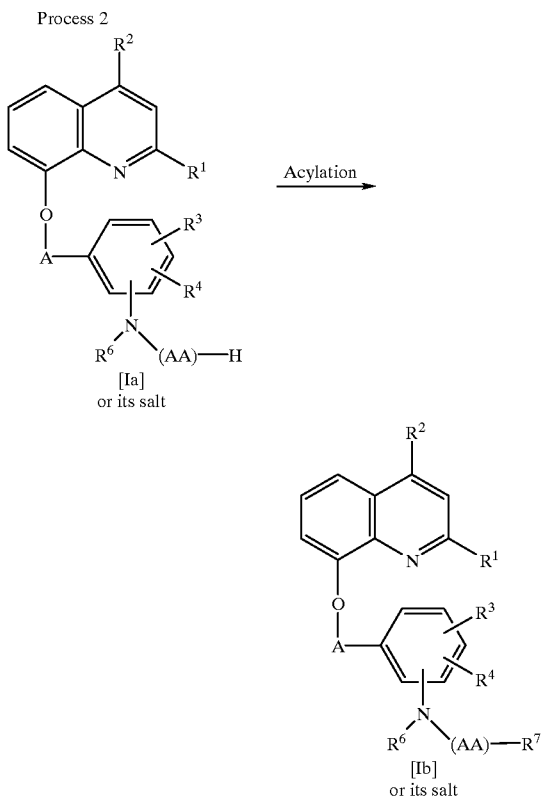

Process 2

[Ia] or its salt

[Ib] or its salt wherein

R⁶ is hydrogen or lower alkyl,

R⁷ is acyl, (AA) is amino acid residue,

X is a leaving group, and

R¹, R², R³, R⁴, R⁵ and A are each as defined above.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

In this respect, the term "lower" in lower alkenyl moieties in the various definitions is intended to mean a group having 2 to 6 carbon atoms.

Further, the term "lower" in ar(lower)alkenoyl moiety, heterocyclic(lower)alkenoyl moiety and pyridyl(lower) alkenoyl moiety in the various definitions is intended to mean a group having 3 to 6 carbon atoms.

Suitable "lower alkyl" and lower alkyl moiety such as in the term "lower alkylcarbamoyl", etc., may be straight or branched one such as methyl, ethyl, propyl, isopropyl, butyl, isobutyl, tert-butyl, pentyl, hexyl or the like, in which preferable one is $C_1$–$C_4$ alkyl such as methyl, ethyl, propyl, isobutyl or tert-butyl.

Suitable "halogen" may be fluorine, chlorine, bromine and iodine.

Suitable "acyl" and acyl moiety in the term "acylamino" may be substituted or unsubstituted alkanoyl such as alkanoyl [e.g. formyl, acetyl, propionyl, butyryl, isobutyryl, valeryl, isovaleryl, pivaloyl, hexanoyl, heptanoyl, 3,3-dimethylbutyryl, etc.], halo(lower)alkanoyl [e.g. chloroacetyl, trifluoroacetyl, bromoacetyl, bromobutyryl, heptafluorobutyryl, etc.], hydroxy(lower)alkanoyl [e.g. glycoloyl, lactoyl, 3-hydroxypropionyl, glyceroyl, etc.], lower alkylsulfonyloxy(lower)alkanoyl [e.g. mesyloxyacetyl, ethylsulfonyloxyacetyl, mesyloxypropionyl, etc.], lower alkoxy(lower)alkanoyl [e.g. methoxyacetyl, ethoxyacetyl, methoxypropionyl, ethoxypropionyl, propoxypropionyl, methoxybutyryl, etc.], lower alkylthio(lower)alkanoyl [e.g. methylthioacetyl, ethylthioacetyl, methylthiopropionyl, ethylthiopropionyl, propylthiopropionyl, methylthiobutyryl, etc.], lower alkanoyloxy(lower)alkanoyl [e.g. acetyloxyacetyl, acetyloxypropionyl, propionyloxyacetyl, etc.], aryloxy (lower)alkanoyl [e.g. phenyloxyacetyl, phenyloxypropionyl, tolyloxyacetyl, naphthyloxyacetyl, etc.], aroyl(lower) alkanoyl [e.g. phenyloxalyl, benzoylacetyl, benzoylpropionyl, etc.], carboxy(lower)alkanoyl [e.g. oxalo, carboxyacetyl, 3-carboxypropionyl, 3-carboxybutyryl, 4-carboxybutyryl, 4-carboxyvaleryl, etc.], esterified carboxy (lower)alkanoyl, for example, lower alkoxycarbonyl(lower) alkanoyl [e.g. methoxycarbonylacetyl, ethoxycarbonylacetyl, methoxycarbonylpropionyl, ethoxycarbonylpropionyl, etc.], carbamoyl(lower)alkanoyl [e.g. carbamoylacetyl, carbamoylpropionyl, etc.], lower alkylcarbamoyl(lower)alkanoyl [e.g. methylcarbamoylacetyl, methylcarbamoylpropionyl, ethylcarbamoylpropionyl, dimethylcarbamoylpropionyl, (N-methyl-N-ethylcarbamoyl)propionyl, etc.], ar(lower) alkanoyl [e.g. phenylacetyl, tolylacetyl, naphthylacetyl, 2-phenylpropionyl, 3-phenylpropionyl, 4-phenylbutyryl, tritylcarbonyl, etc.], heterocyclic(lower)alkylcarbamoyl-ar (lower)alkanoyl [e.g. pyridylmethylcarbamoylphenylpropionyl, furylmethylcarbamoylphenylpropionyl, etc.], optionally substituted heterocyclic(lower)alkanoyl [e.g. morpholinoacetyl, thiomorpholinoacetyl, morpholinopropionyl, thiomorpholinopropionyl, piperidinopropionyl, piperazinylpropionyl, pyridylacetyl, pyrrolidinylpropionyl, imidazolidinylpropionyl, piperidinoacetyl, pyrrolidinylacetyl, hexamethyleneiminoacetyl, hexamethyleneiminopropionyl, imidazolylacetyl, furylacetyl, thienylacetyl, methylpiperazinylacetyl, pyridylpiperazinylacetyl, etc.], heterocyclicthio(lower)alkanoyl [e.g. pyridylthioacetyl, pyrimidinylthioacetyl, imidazolylthiopropionyl, etc.], etc., lower alkenoyl [e.g. acryloyl, crotonoyl, isocrotonoyl, 3-butenoyl, 3-pentenoyl, 4-pentenoyl, methacryloyl, etc.], lower alkynoyl [e.g. propioloyl, 2-butynoyl, 3-butynoyl, etc.], cyclo(lower)alkylcarbonyl [e.g. cyclopropylcarbonyl, cyclobutylcarbonyl, cyclopentylcarbonyl, cyclohexylcarbonyl, etc.], cyclo(lower)alkenylcarbonyl [e.g. cyclopentenylcarbonyl, cyclohexenylcarbonyl, etc.], carboxy, esterified carboxy such as lower alkoxycarbonyl [e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, etc.], aryloxycarbonyl [e.g. phenoxycarbonyl, etc.], etc., substituted or unsubstituted aroyl such as aroyl [e.g. benzoyl, toluoyl, xyloyl, naphthoyl, etc.], lower alkoxyaroyl [e.g. methoxybenzoyl, etc.], haloaroyl [e.g. chlorobenzoyl, fluorobenzoyl, etc.], acylaroyl, for example, lower alkoxy-carbonylaroyl [e.g. methoxycarbonylbenzoyl, etc.], etc., substituted or unsubstituted ar(lower)alkenoyl such as ar(lower)alkenoyl [e.g. cinnamoyl, allocinnamoyl, α-methylcinnamoyl, 4-methylcinnamoyl, etc.], lower alkoxy-ar(lower)alkenoyl [e.g. methoxycinnamoyl, ethoxycinnamoyl, dimethoxycinnamoyl, etc.], lower alkylenedioxy-ar(lower)alkenoyl [e.g. methylenedioxycinnamoyl, ethylenedioxycinnamoyl, etc.], nitro-ar(lower)alkenoyl [e.g. nitrocinnamoyl, etc.], cyano-ar(lower)alkenoyl [e.g. cyanocinnamoyl, etc.], halo-ar(lower)alkenoyl [e.g. chlorocinnamoyl, fluorocinnamoyl, etc.], hydroxy-ar(lower)alkenoyl [e.g. hydroxycinnamoyl, etc.], hydroxy(lower)alkoxy-ar(lower)alkenoyl [e.g. hydroxymethoxycinnamoyl, hydroxyethoxycinnamoyl, etc.], amino(lower)alkoxy-ar(lower)alkenoyl [e.g. aminoethoxycinnamoyl, etc.], lower alkylamino(lower)alkoxy-ar(lower)alkenoyl [e.g. methylaminomethoxycinnamoyl, dimethylaminoethoxycinnamoyl, etc.], heterocyclic(lower)alkoxy-ar(lower)alkenoyl [e.g. pyridylmethoxycinnamoyl, etc.], optionally substituted heterocyclic-ar(lower)alkenoyl [e.g. morpholinocinnamoyl, methylpiperazinylcinnamoyl, pyrrolidinylcinnamoyl, oxopyrrolidinylcinnamoyl, oxopiperidinocinnamoyl, dioxopyrrolidinylcinnamoyl, oxooxazolidinylcinnamoyl, pyrrolylcinnamoyl, tetrazolylcinnamoyl, etc.], heterocyclic(lower)alkyl-ar(lower)alkenoyl [e.g. pyridylmethylcinnamoyl, pyridylethylcinnamoyl, quinolylethylcinnamoyl, etc.], heterocyclic(lower)alkenyl-ar(lower)alkenoyl [e.g. pyridylvinylcinnamoyl, quinolylvinylcinnamoyl, etc.], amino-ar(lower)alkenoyl [e.g. aminocinnamoyl, etc.], lower alkylamino-ar(lower)alkenoyl [e.g. methylaminocinnamoyl, dimethylaminocinnamoyl, etc.], acylamino-ar(lower)alkenoyl, for example, lower aLkanoylamino-ar(lower)alkenoyl [e.g. acetylaminocinnamoyl, propionylaminocinnamoyl, isobutyrylaminocinnamoyl, 4-acetylamino-3-methylcinnamoyl, etc.], cycloalkyl(lower)alkanoylamino-ar(lower)alkenoyl [e.g. cyclopentylacetylaminocinnamoyl, cyclohexylacetylaminocinnamoyl, adamantylacetylaminocinnamoyl, etc.], cycloalkylcarbonylamino-ar(lower)alkenoyl [e.g. cyclopropylcarbonylaminocinnamoyl, cyclopentylcarbonylaminocinnamoyl, cyclohexylcarbonylaminocinnamoyl, adamantylcarbonylaminocinnamoyl, etc.], lower alkenoylamino-ar(lower)alkenoyl [e.g. acryloylaminocinnamoyl, crotonoylaminocinnamoyl, etc.], lower alkoxycarbonylamino-ar(lower)alkenoyl [e.g. methoxycarbonylaminocinnamoyl, ethoxycarbonylaminocinnamoyl, etc.], hydroxy(lower)alkanoylamino-ar(lower)alkenoyl [e.g. hydroxyacetylaminocinnamoyl, hydroxypropionylaminocinnamoyl, etc.], lower alkoxy(lower)alkanoylamino-ar(lower)alkenoyl [e.g. methoxyacetylaminocinnamoyl, methoxypropionylaminocinnamoyl, etc.], halo(lower)alkanoylamino-ar(lower)alkenoyl [e.g. chloroacetylaminocinnamoyl, bromobutyrylaminocinnamoyl, trifluoroacetylaminocinnamoyl, etc.], amino(lower)alkanoylamino-ar(lower)alkenoyl [e.g. aminoacetylaminocinnamoyl, aminopropionylaminocinnamoyl, etc.], lower alkylamino(lower)alkanoylamino-ar(lower)alkenoyl [e.g. methylaminoacetylaminocinnamoyl, dimethylaminoacetylaminocinnamoyl, etc.], lower alkylamino(lower)alkanoylamino-ar(lower)alkenoyl [e.g. acetylaminoacetylaminocinnamoyl, acetylaminopropionylaminocinnamoyl, etc.], carboxy(lower)alkanoylamino-ar(lower)alkenoyl [e.g. carboxyacetylaminocinnamoyl, carboxypropionylaminocinnamoyl, etc.], lower alkoxycarbonyl(lower)alkanoylamino-ar(lower)alkenoyl [e.g. ethoxycarbonylacetylaminocinnamoyl, ethoxycarbonylpropionylaminocinnamoyl, etc.], lower alkoxycarbonyl(lower)alkenoylamino-ar(lower)alkenoyl [e.g. ethoxycarbonylacryloylaminocinnamoyl, etc.], halo(lower)alkoxycarbonylamino-ar(lower)alkenoyl [e.g. chloroethoxycarbonylaminocinnamoyl, etc.], optionally substituted heterocyclic(lower)alkanoylamino-ar(lower)alkenoyl [e.g. pyridylacetylaminocinnamoyl, thienylacetylaminocinnamoyl, methylpyrrolylacetylaminocinnamoyl, etc.], aroylamino-ar(lower)alkenoyl [e.g. benzoylaminocinnamoyl, etc.], optionally substituted heterocycliccarbonylamino-ar(lower)alkenoyl [e.g. pyridylcarbonylaminocinnamoyl, morpholinocarbonylaminocinnamoyl, furylcarbonylaminocinnamoyl, thienylcarbonylaminocinnamoyl, oxazolylcarbonylaminocinnamoyl, methyloxazolylcarbonylaminocinnamoyl, dimethylisoxazolylcarbonylaminocinnamoyl, imidazolylcarbonylaminocinnamoyl, methylimidazolylcarbonylaminocinnamoyl, piperidylcarbonylaminocinnamoyl, ethylpiperidylcarbonylaminocinnamoyl, acetylpiperidylcarbonylaminocinnamoyl, pyrrolidinylcarbonylaminocinnamoyl, acetylpyrrolidinylcarbonylaminocinnamoyl, tert-butoxycarbonylpyrrolidinylcarbonylaminocinnamoyl, etc.], lower alkylsulfonylamino-ar(lower)alkenoyl [e.g. mesylaminocinnamoyl, ethylsulfonylaminocinnamoyl, etc.], etc., N-(lower alkanoyl)-N-(lower alkyl)amino-ar(lower)alkenoyl [e.g. N-acetyl-N-methylaminocinnamoyl, N-acetyl-N-ethylaminocinnamoyl, N-propionyl-N-methylaminocinnamoyl, etc.], N-[lower alkoxy(lower)alkanoyl]-N-(lower alkyl)amino-ar(lower)alkenoyl [e.g. N-methoxyacetyl-N-methylaminocinnamoyl, N-methoxypropionyl-N-methylaminocinnamoyl, etc.], N-(lower alkanoyl)-N-[heterocyclic(lower)alky]amino-ar(lower)alkenoyl [e.g. N-acetyl-N-pyridylmethylaminocinnamoyl, etc.], N-(lower alkanoyl)-N-[lower alkoxy(lower)alkyl]amino-ar(lower)alkenoyl [e.g. N-acetyl-N-methoxymethylaminocinnamoyl, N-acetyl-N-methoxymethylaminocinnamoyl, N-propionyl-N-methoxyethylaminocinnamoyl, etc.], N-(lower alkanoyl)-N-[lower alkoxycarbonyl(lower)alkyl]-amino-ar(lower)alkenoyl [e.g. N-acetyl-N-tert-butoxycarbonylmethylaminocinnamoyl, N-acetyl-N-tert-butoxycarbonylethylaminocinnamoyl, N-propionyl-N-tert-butoxycarbonylmethylaminocinnamoyl, etc.], N-(lower alkanoyl)-N-[carboxy(lower)alkyl]amino-ar(lower)alkenoyl [e.g. N-acetyl-N-carboxymethylaminocinnamoyl, N-acetyl-N-carboxyethylaminocinnamoyl, N-propionyl-N-carboxymethylaminocinnamoyl, etc.], N-[lower alkoxy(lower)alkanoyl]-N-[heterocyclic(lower)alkyl]amino-ar(lower)alkenoyl [e.g. N-methoxyacetyl-N-pyridylmethylaminocinnamoyl, N-methoxypropionyl-N-pyridylmethylaminocinnamoyl, etc.], N-[heterocycliccarbonyl]-N-[lower alkoxy(lower)alkyl]amino-ar(lower)alkenoyl [e.g. N-pyridylcarbonyl-N-methoxymethylaminocinnamoyl, N-pyridylcarbonyl-N-methoxyethylaminocinnamoyl, N-thienylcarbonyl-N-methoxyethylaminocinnamoyl, etc.], ureido-ar(lower)alkenoyl [e.g. ureidocinnamoyl, etc.], lower alkylureido-ar(lower)alkenoyl [e.g. methylureidocinnamoyl, ethylureidocinnamoyl, dimethylureidocinnamoyl, etc.], heterocyclicureido-ar(lower)alkenoyl [e.g. pyridylureidocinnamoyl, pyrimidinylureidocinnamoyl, thienylureidocinnamoyl, etc.], acyl-ar(lower)alkenoyl, for example, lower alkanoyl-ar(lower)alkenoyl [e.g.

formylcinnamoyl, acetylcinnamoyl, propionylcinnamoyl, etc.], carboxy-ar(lower)alkenoyl [e.g. carboxycinnamoyl, etc], lower alkoxycarbonyl-ar(lower)alkenoyl [e.g. methoxycarbonylcinnamoyl, ethoxycarbonylcinnamoyl, etc.], carbamoyl-ar(lower)alkenoyl [e.g. carbamoylcinnamoyl, etc.], lower alkylcarbamoyl-ar(lower)alkenoyl [e.g. methylcarbamoylcinnamoyl, ethylcarbamoylcinnamoyl, dimethylcarbamoylcinnamoyl, propylcarbamoylcinnamoyl, isopropylcarbamoylcinnamoyl, diethylcarbamoylcinnamoyl, N-methyl-N-ethylcarbamoylcinnamoyl, etc.], (lower alkylcarbamoyl)(lower alkoxy)-ar(lower)alkenoyl [e.g. 4-methylcarbamoyl-3-methoxycinnamoyl, 4-dimethylcarbamoyl-3-methoxycinnamoyl, etc.], hydroxy(lower)alkylcarbamoyl-ar(lower)alkenoyl [e.g. hydroxyethylcarbamoylcinnamoyl, bis(hydroxyethyl)carbamoylcinnamoyl, etc.], N-[hydroxy(lower)alkyl]-N-(lower alkyl)carbamoyl-ar(lower)alkenoyl [e.g. N-hydroxyethyl-N-methylcarbamoylcinnamoyl, etc.], lower alkoxy(lower)alkylcarbamoyl-ar(lower)alkenoyl [e.g. methoxymethylcarbamoylcinnamoyl, methoxyethylcarbamoylcinnamoyl, bis(methoxyethyl)carbamoylcinnamoyl, ethoxyethylcarbamoylcinnamoyl, methoxypropylcarbamoylcinnamoyl, bis(ethoxyethyl)carbamoylcinnamoyl, etc.], N-[lower alkoxy(lower)alkyl]-N-(lower alkyl)carbamoyl-ar(lower)alkenoyl [e.g. N-methoxyethyl-N-methylcarbamoylcinnamoyl, N-ethoxyethyl-N-methylcarbamoylcinnamoyl, etc.], heterocyclic(lower)alkylcarbamoyl-ar(lower)alkenoyl [e.g. pyridylmethylcarbamoylcinnamoyl, furylmethylcarbamoylcinnamoyl, thienylmethylcarbamoylcinnamoyl, etc.], N-[heterocyclic(lower)alkyl]-N-(lower alkyl)carbamoyl-ar(lower)alkenoyl [e.g. N-pyridylmethyl-N-methylcarbamoylcinnamoyl, etc.], heterocycliccarbamoyl-ar(lower)alkenoyl [e.g. morpholinylcarbamoylcinnamoyl, thienylcarbamoylcinnamoyl, pyridylcarbamoylcinnamoyl, pyrimidinylcarbamoylcinnamoyl, tetrazolylcarbamoylcinnamoyl, etc.], optionally substituted heterocycliccarbonyl-ar(lower)alkenoyl [e.g. morpholinocarbonylcinnamoyl, pyrrolidinylcarbonylcinnamoyl, piperidinocarbonylcinnamoyl, tetrahydropyridylcarbonylcinnamoyl, methylpiperazinylcarbonylcinnamoyl, etc.], lower alkenylcarbamoyl-ar(lower)alkenoyl [e.g. vinylcarbamoylcinnamoyl, allylcarbamoylcinnamoyl, methylpropenylcarbamoylcinnamoyl, etc.], lower alkynylcarbamoyl-ar(lower)alkenoyl [e.g. ethynylcarbamoylcinnamoyl, propynylcarbamoylcinnamoyl, etc.], amino(lower)alkylcarbamoyl-ar(lower)alkenoyl [e.g. aminomethylcarbamoylcinnamoyl, aminoethylcarbamoylcinnamoyl, etc.], lower alkylamino(lower)alkylcarbamoyl-ar(lower)alkenoyl [e.g. methylaminomethylcarbamoylcinnamoyl, methylaminoethylcarbamoylcinnamoyl, ethylaminoethylcarbamoylcinnamoyl, dimethylaminoethylcarbamoylcinnamoyl, etc.], lower alkylcarbamoyloxy(lower)alkylcarbamoyl-ar(lower)alkenoyl [e.g. methylcarbamoyloxymethylcarbamoylcinnamoyl, methylcarbamoyloxyethylcarbamoylcinnamoyl, ethylcarbamoyloxyethylcarbamoylcinnamoyl, dimethylcarbamoyloxyethylcarbamoylcinnamoyl, etc.], lower alkylcarbamoyl(lower)alkylcarbamoyl-ar(lower)alkenoyl [e.g. methylcarbamoylmethylcarbamoylcinnamoyl, methylcarbamoylethylcarbamoylcinnamoyl, ethylcarbamoylethylcarbamoylcinnamoyl, dimethylcarbamoylethylcarbamoylcinnamoyl, etc.], lower alkoxycarbonyl(lower)alkylcarbamoyl-ar(lower)alkenoyl (e.g. methoxycarbonylmethylcarbamoylcinnamoyl, methoxycarbonylethylcarbamoylcinnamoyl, ethoxycarbonylmethylcarbamoylcinnamoyl, ethoxycarbonylethylcarbamoylcinnamoyl, etc.], carboxy(lower)alkylcarbamoyl-ar(lower)alkenoyl [e.g. carboxymethylcarbamoylcinnamoyl, carboxyethylcarbamoylcinnamoyl, etc.], [lower alkylcarbamoyl-ar(lower)alkyl]carbamoyl-ar(lower)alkenoyl [e.g. (methylcarbamoyl-phenethyl)carbamoylcinnamoyl, (ethylcarbamoyl-phenethyl)carbamoylcinnamoyl, etc.], [lower alkoxycarbonyl-ar(lower)alkyl]carbamoyl-ar(lower)alkenoyl [e.g. (methoxycarbonyl-phenethyl)carbamoylcinnamoyl, (ethoxycarbonyl-phenethyl)carbamoylcinnamoyl, etc.], [carboxy-ar(lower)alkyl]carbamoyl-ar(lower)alkenoyl [e.g. carboxy-phenethyl)carbamoylcinnamoyl, etc.], N-[lower alkylcarbamoyl(lower)alkyl]-N-(lower alkyl)carbamoyl-ar(lower)alkenoyl [e.g. N-(methylcarbamoylmethyl)-N-methylcarbamoylcinnamoyl, N-(methylcarbamoylethyl)-N-methylcarbamoylcinnamoyl, N-(ethylcarbamoylethyl)-N-methylcarbamoylcinnamoyl, N-(dimethylcarbamoylethyl)-N-methylcarbamoylcinnamoyl, etc.], N-[lower alkoxycarbonyl(lower)alkyl]-N-(lower alkyl)carbamoyl-ar(lower)alkenoyl [e.g. N-methoxycarbonylmethyl-N-methylcarbamoylcinnamoyl, N-methoxycarbonylethyl-N-methylcarbamoylcinnamoyl, N-ethoxycarbonylmethyl-N-methylcarbamoylcinnamoyl, N-ethoxycarbonylethyl-N-methylcarbamoylcinnamoyl, etc.], N-[carboxy(lower)alkyl]-N-(lower alkyl)carbamoyl-ar(lower)alkenoyl [e.g. N-carboxymethyl-N-methylcarbamoylcinnamoyl, N-carboxyethyl-N-methylcarbamoylcinnamoyl, etc.], arylcarbamoyl-ar(lower)alkenoyl [e.g. phenylcarbamoylcinnamoyl, naphthylcarbamoylcinnamoyl, etc.], etc., etc., ar(lower)alkynoyl [e.g. phenylpropioloyl, etc.], substituted or unsubstituted heterocyclic(lower)alkenoyl such as heterocyclic(lower)alkenoyl [e.g. morpholinylacryloyl, pyridylacryloyl, thienylacryloyl, etc.], heterocyclic(lower)alkyl-heterocyclic(lower)alkenoyl [e.g. pyridylmethylpyridylacryloyl, pyridylethylpyridylacryloyl, quinolylethylpyridylacryloyl, etc.], heterocyclic(lower)alkenyl-heterocyclic(lower)alkenoyl [e.g. pyridylvinylpyridylacryloyl, quinolylvinylpyridylacryloyl, etc.], amino-heterocyclic(lower)alkenoyl [e.g. aminopyridylacryloyl, etc.], lower alkylamino-heterocyclic(lower)alkenoyl [e.g. methylaminopyridylacryloyl, dimethylaminopyridylacryloyl, etc.], acylamino-heterocyclic(lower)alkenoyl, for example, lower alkanoylamino-heterocyclic(lower)alkenoyl [e.g. acetylaminopyridylacryloyl, propionylaminopyridylacryloyl, etc.], lower alkenoylamino-heterocyclic(lower)alkenoyl [e.g. acryloylaminopyridylacryloyl, crotonoylaminopyridylacryloyl, etc.], heterocyclic(lower)alkanoylamino-heterocyclic(lower)alkenoyl [e.g. pyridylacetyiaminopyridylacryloyl, thienylacetylaminopyridylacryloyl, etc.], optionally substituted heterocycliccarbonylamino-heterocyclic(lower)alkenoyl [e.g. pyridylcarbonylaminopyridylacryloyl, furylcarbonylaminopyridylacryloyl, methylpyridylcarbonylaminopyridylacryloyl, etc.], lower alkanoylamino(lower)alkanoylamino-heterocyclic(lower)alkenoyl [e.g. acetylaminoacetylaminopyridylacryloyl, acetylaminopropionylaminopyridylacryloyl, etc.], lower alkoxycarbonyl(lower)alkanoylamino-heterocyclic(lower) alkenoyl [e.g. ethoxycarbonylacetylaminopyridylacryloyl, ethoxycarbonylpropionylaminopyridylacryloyl, etc.], lower alkoxy(lower)alkanoylamino-heterocyclic(lower)alkenoyl [e.g. methoxyacetylaminopyridylacryloyl, methoxypropionylaminopyridylacryloyl, ethoxypropionylaminopyridylacryloyl, etc.], etc., lower alkylureido-heterocyclic(lower)alkenoyl [e.g. methylureidopyridypacryloyl, etc.], acyl-heterocyclic (lower)alkenoyl, for example, carboxy-heterocyclic(lower) alkenoyl [e.g. carboxypyridylacryloyl, etc.], lower alkoxycarbonyl-heterocyclic(lower)alkenoyl [e.g. ethoxycarbonylpyridylacryloyl, etc.], lower alkanoyl-heterocyclic(lower)alkenoyl [e.g. acetylpyridylacryloyl, acetyltetrahydroquinolylacryloyl, etc.], lower alkylcarbamoyl-heterocyclic(lower)alkenoyl [e.g. methylcarbamoylpyridylacryloyl, ethylcarbamoylpyridylacryloyl, dimethylcarbamoylpyridylacryloyl, diethylcarbamoylpyridylacryloyl, isopropylcarbamoylpyridylacryloyl, N-ethyl-N-methylcarbamoylpyridylacryloyl, etc.], lower alkoxy(lower) alkylcarbamoyl-heterocyclic(lower)alkenoyl [e.g. methoxymethylcarbamoylpyridylacryloyl, methoxyethylcarbamoylpyridylacryloyl, methoxypropylcarbamoylpyridylacryloyl, ethoxyethylcarbamoylpyridylacryloyl, bis(methoxyethyl) carbamoylpyridylacryloyl, etc.], hydroxy(lower) alkylcarbamoyl-heterocyclic(lower)alkenoyl [e.g. hydroxymethylcarbamoylpyridylacryloyl, hydroxyethylcarbamoylpyridylacryloyl, bis(hydroxyethyl) carbamoylpyridylacryloyl, etc.], heterocycliccarbamoyl-heterocyclic(lower)alkenoyl [e.g. pyridylcarbamoylpyridylacryloyl, morpholinylcarbamoylpyridylacryloyl, thienylcarbamoylpyridylacryloyl, pyrimidinylcarbamoylpyridylacryloyl, etc.], heterocyclic (lower)alkylcarbamaoyl-heterocyclic(lower)alkenoyl [e.g. pyridylmethylcarbamoylpyridylacryloyl, furylmethylcarbamoylpyridylacryloyl, thienylmethylcarbamoylpyridylacryloyl, etc.], heterocycliccarbonyl-heterocyclic(lower)alkenoyl [e.g. morpholinocarbonylpyridylacryloyl, pyrrolidinylcarbonylpyridylacryloyl, piperidinocarbonylpyridylacryloyl, etc.], lower alkenylcarbamoyl-heterocyclic(lower)alkenoyl [e.g. vinylcarbamoylpyridylacryloyl, allylcarbamoylpyridylacryloyl, etc.], lower alkynylcarbamoyl-heterocyclic(lower)alkenoyl [e.g. ethynylcarbamoylpyridylacryloyl, propynylcarbamoylpyridylacryloyl, etc.], etc., etc., heterocycliccarbonyl which may be substituted with substituent [e.g. furoyl, thenoyl, nicotinoyl, methylnicotinoyl, isonicotinoyl, morpholinocarbonyl, piperidinocarbonyl, 4-methyl-1-piperazinylcarbonyl, 4-ethyl-1-piperazinylcarbonyl, dimethylaminopiperidinocarbonyl, 4-methylcarbamoyl-1-piperazinylcarbonyl, 1,2,3,6-tetrahydropyridylcarbonyl, pyrrolidinylcarbonyl, indolylcarbonyl, etc.], aryloxycarbonyl which may be substituted with nitro [e.g. phenyloxycarbonyl, nitrophenyloxycarbonyl, etc.], ar(lower)alkoxycarbonyl which may be substituted with nitro [e.g. benzyloxycarbonyl, nitrobenzyloxycarbonyl, etc.], substituted or unsubstituted carbamoyl or thiocarbamoyl such as carbamoyl, lower alkylcarbamoyl [e.g. methylcarbamoyl, ethylcarbamoyl, propylcarbamoyl, isopropylcarbamoyl, butylcarbamoyl, isobutylcarbamoyl, tert-butylcarbamoyl, pentylcarbamoyl, dimethylcarbamoyl, diethylcarbamoyl, N-ethyl-N-methylcarbamoyl, etc.], carboxy(lower) alkylcarbamoyl [e.g. carboxymethylcarbamoyl, carboxyethylcarbamoyl, etc.], esterified carboxy(lower) alkylcarbamoyl, for example, lower alkoxycarbonyl(lower) alkylcarbamoyl [e.g. methoxycarbonylmethylcarbamoyl, ethoxycarbonylmethylcarbamoyl, ethoxycarbonylethylcarbamoyl, etc.], lower alkenylcarbamoyl [e.g. vinylcarbamoyl, allylcarbamoyl, etc.], cyclo(lower) alkylcarbamoyl [e.g. cyclopropylcarbamoyl, cyclobutylcarbamoyl, cyclopentylcarbamoyl, cyclohexylcarbamoyl, etc.], halo(lower)alkanoylcarbamoyl [e.g. trichloroacetylcarbamoyl, etc.], substituted or unsubstituted arylcarbamoyl, for example, arylcarbamoyl [e.g. phenylcarbamoyl, tolylcarbamoyl, xylylcarbamoyl, naphthylcarbamoyl, ethylphenylcarbamoyl, etc.], arylthiocarbamoyl [e.g. phenylthiocarbamoyl, etc.], lower alkoxyarylcarbamoyl [e.g. methoxyphenylcarbamoyl, etc.], haloarylcarbamoyl [e.g. fluorophenylcarbamoyl, chlorophenylcarbamoyl, etc.], halo(lower)alkylarylcarbamoyl [e.g. trifluoromethylphenylcarbamoyl, etc.], nitro-arylcarbamoyl [e.g. nitrophenylcarbamoyl, etc.], cyano-arylcarbamoyl [e.g. cyanophenylcarbamoyl, etc.], hydroxy(lower)alkyl-arylcarbamoyl [e.g. hydroxymethylphenylcarbamoyl, hydroxyethylphenylcarbamoyl, etc.], amino-arylcarbamoyl [e.g. aminophenylcarbamoyl, etc.], lower alkylaminoarylcarbamoyl [e.g. methylaminophenylcarbamoyl, ethylaminophenylcarbamoyl, dimethylaminophenylcarbamoyl, etc.], lower alkanoylaminoarylcarbamoyl [e.g. acetylaminophenylcarbamoyl, propionylaminophenylcarbamoyl, etc.], N-(lower alkanoyl)-N-(lower alkyl)amino-arylcarbamoyl [e.g. N-acetyl-N-methylaminophenylcarbamoyl, N-propionyl-N-methylaminophenylcarbamoyl, etc.], lower alkoxy(lower) alkanoylamino-arylcarbamoyl [e.g. methoxyacetylaminophenylcarbamoyl, methoxypropionylaminophenylcarbamoyl, etc.], lower alkoxycarbonyl(lower)alkanoylamino-arylcarbamoyl [e.g. ethoxycarbonylacetylaminophenylcarbamoyl, methoxycarbonylpropionylaminophenylcarbamoyl, etc.], carboxyamino-arylcarbamoyl [e.g. carboxyaminophenylcarbamoyl, etc.], lower alkoxycarbonylamino-arylcarbamoyl [e.g. ethoxycarbonylaminophenylcarbamnoyl, etc.], aroylaminoarylcarbamoyl [e.g. benzoylaminophenylcarbamoyl, etc.], heterocycliccarbonylamino-arylcarbamoyl [e.g. pyridylcarbonylaminophenylcarbamoyl, furylcarbonylaminophenylcarbamoyl, morpholinocarbonylaminophenylcarbamoyl, etc.], heterocyclic(lower)alkanoylamino-arylcarbamoyl [e.g. pyridylacetylaminophenylcarbamoyl, thienylacetylaminophenylcarbamoyl, etc.], ureidoarylcarbamoyl [e.g. ureidophenylcarbamoyl, etc.], lower alkylureido-arylcarbamoyl [e.g. methylureidophenylcarbamoyl, ethylureidophenylcarbamoyl, etc.], hydroxyimino(lower) alkyl-arylcarbamoyl [e.g. hydroxyiminoethylphenylcarbamoyl, etc.], lower alkoxyimino(lower)alkyl-arylcarbamoyl [e.g. methoxyiminoethylphenylcarbamoyl, etc.], lower alkylhydrazono(lower)alkyl-arylcarbamoyl [e.g. methylhydrazonoethylphenylcarbamoyl, dimethylhydrazonoethylphenylcarbamoyl, etc.], optionally substituted heterocyclic-arylcarbamoyl [e.g. oxopyrrolidinylphenylcarbamoyl, oxopiperidinophenylcarbamoyl, dioxopyrrolidinylphenylcarbamoyl, oxooxazolidinylphenylcarbamoyl, pyrrolylphenylcarbamoyl, etc.], acyl-arylcarbamoyl, for example, carboxy-arylcarbamoyl [e.g. carboxyphenylcarbamoyl, etc.], lower alkoxycarbonyl-arylcarbamoyl [e.g. ethoxycarbonylphenylcarbamoyl, etc.], heterocycliccarbonyl-arylcarbamoyl [e.g. morpholinocarbonylphenylcarbamoyl, pyrrolidinylcarbonylphenylcarbamoyl, piperidinocarbonylphenylcarbamoyl, 1,2,3,6-tetrahydropyridylcarbonylphenylcarbamoyl, piperazinylcarbonylphenylcarbamoyl, thiomorpholinocarbonylphenylcarbamoyl, etc.], heterocycliccarbonyl-arylcarbamoyl substituted with lower alkyl [e.g. methylpiperazinylcarbonylphenylcarbamoyl, ethylpiperazinylcarbonylphenylcarbamoyl, etc.], heterocycliccarbonyl-arylcarbamoyl substituted with aryl [e.g. phenylpiperazinylcarbonylphenylcarbamoyl, etc.], heterocycliccarbonyl-arylcarbamoyl substituted with a heterocyclic group (e.g. pyridylpiperazinylcarbonyl-phenylcarbamoyl, etc.l, heterocycliccarbonyl-arylcarbamoyl substituted with lower alkanoyl [e.g. acetylpiperazinyl-carbonylphenylcarbamoyl, etc.], heterocycliccarbonyl-arylcarbamoyl substituted with lower alkoxycarbonyl [e.g. ethoxycarbonylpiperazinylcarbonylphenylcarbamoyl, etc.], heterocycliccarbonyl-arylcarbamoyl substituted with lower alkylamino [e.g. methylaminopiperazinylcarbonylphenylcarbamoyl, dimethylaminopiperidinocarbonylphenylcarbamoyl, etc.], heterocycliccarbonyl-arylcarbamoyl substituted with lower alkylcarbamoyl [e.g. methylcarbamoylpiperazinylcarbonylphenylcarbamoyl, etc.], carbamoyl-arylcarbamoyl [e.g. carbamoylphenylcarbamoyl, etc.], lower alkylcarbamoyl-arylcarbamoyl [e.g. methylcarbamoylphenylcarbamoyl, ethylcarbamoylphenylcarbamoyl, propylcarbamoylphenylcarbamoyl, dimethylcarbamoylphenylcarbamoyl, diethylcarbamoylphenylcarbamoyl, N-ethyl-N-methylcarbamoylphenylcarbamoyl, N-isopropyl-N-methylcarbamoylphenylcarbamoyl, etc.], hydroxy(lower)alkylcarbamoyl-arylcarbamoyl [e.g. hydroxymethylcarbamoylphenylcarbamoyl, hydroxyethylcarbamoylphenylcarbamoyl, bis(hydroxyethyl)carbamoylphenylcarbamoyl, etc.], N-[hydroxy(lower)alkyl]-N-(lower alkyl)carbamoyl-arylcarbamoyl [e.g. N-(hydroxyethyl)-N-methylcarbamoylphenylcarbamoyl, etc.], lower alkoxy(lower)alkylcarbamoyl-arylcarbamoyl [e.g. methoxymethylcarbamoylphenylcarbamoyl, methoxyethylcarbamoylphenylcarbamoyl, ethoxyethylcarbamoylphenylcarbamoyl, bis(methoxyethyl)carbamoylphenylcarbamoyl, bis(ethoxyethyl)carbamoylphenylcarbamoyl, etc.], N-[lower alkoxy(lower)alkyl]-N-(lower alkyl)carbamoyl-arylcarbamoyl [e.g. N-(methoxyethyl)-N-methylcarbamoylphenylcarbamoyl, N-(methoxypropyl)-N-methylcarbamoylphenylcarbamoyl, etc.], lower alkylamino(lower)alkylcarbamoyl-arylcarbamoyl [e.g. methylaminoethylcarbamoylphenylcarbamoyl, dimethylaminoethylcarbamoylphenylcarbamoyl, etc.], N-[lower alkylamino(lower)alkyl]-N-(lower alkyl)carbamoylarylcarbamoyl [e.g. N-(dimethylaminoethyl)-N-methylcarbamoylphenylcarbamoyl, N-(dimethylaminopropyl)-N-methylcarbamoylphenylcarbamoyl, etc.], heterocycliccarbamoyl-arylcarbamoyl [e.g. morpholinylcarbamoylphenylcarbamoyl, thienylcarbamoylphenylcarbamoyl, pyridylcarbamoylphenylcarbamoyl, pyrimidinylcarbamoylphenylcarbamoyl, etc.], N-(heterocyclic)-N-(lower alkyl)carbamoyl-arylcarbamoyl [e.g. N-pyridyl-N-methylcarbamoylphenylcarbamoyl, etc.], heterocyclic(lower)alkylcarbamoyl-arylcarbamoyl [e.g. pyridylmethylcarbamoylphenylcarbamoyl, pyridylethylcarbamoylphenylcarbamoyl, thienylmethylcarbamoylphenylcarbamoyl, etc.], N-[heterocyclic(lower)alkyl]-N-(lower alkyl)carbamoyl-arylcarbamoyl [e.g. N-pyridylmethyl-N-methylcarbamoylphenylcarbamoyl, etc.], N-[heterocyclic(lower)alkyl]-N-[lower alkoxy(lower)alkyl]-carbamoyl-arylcarbamoyl [e.g. N-pyridylmethyl-N-methoxyethylcarbamoylphenylcarbamoyl, etc.], arylcarbamoyl-arylcarbamoyl [e.g. phenylcarbamoylphenylcarbamoyl, etc.], lower alkylaminoarylcarbamoyl-arylcarbamoyl [e.g. dimethylaminophenylcarbamoylphenylcarbamoyl, etc.], lower alkanoyl-arylcarbamoyl [e.g. acetylphenylcarbamoyl, propionylphenylcarbamoyl, etc.], etc., etc., ar(lower)alkylcarbamoyl [e.g. benzylcarbamoyl, phenethylcarbamoyl, etc.], heterocycliccarbamoyl [e.g. furylcarbamoyl, thienylcarbamoyl, pyridylcarbamoyl, quinolylcarbamoyl, isoquinolylcarbamoyl, pyrimidinylcarbamoyl, pyrazolylcarbamoyl, etc.], heterocyclic(lower)alkylcarbamoyl [e.g. pyridylmethylcarbamoyl, pyridylethylcarbamoyl, furylmethylcarbamoyl, thienylmethylcarbamoyl, etc.], arylaminocarbamoyl [e.g. phenylaminocarbamoyl, etc.], aroylcarbamoyl [e.g. benzoylcarbamoyl, etc.], etc., lower alkylsulfonyl [e.g. mesyl, ethylsulfonyl, propylsulfonyl, isopropylsulfonyl, tert-butylsulfonyl, pentylsulfonyl, etc.], arylsulfonyl [e.g. tosyl, phenylsulfonyl, etc.], ar(lower)alkylsulfonyl [e.g. benzylsulfonyl, phenethylsulfonyl, etc.], ar(lower)alkenylsulfonyl [e.g. styrylsulfonyl, cinnamylsulfonyl, etc.], phthaloyl, substituted or unsubstituted amino acid residue mentioned below, or the like.

Suitable "amino acid residue" may include natural or artificial ones, and such amino acid may be glycine, sarcosine, alanine, β-alanine, valine, norvaline, leucine, isoleucine, norleucine, serine, threonine, cysteine, methionine, phenylalanine, phenylglycine, tryptophan, tyrosine, proline, hydroxyproline, glutamic acid, aspartic acid, glutamine, asparagine, lysine, arginine, histidine, ornithine, or the like, in which more preferable one is glycine, sarcosine, alanine, β-alanine and proline, and the most preferable one is glycine. And said amino acid residue may be substituted with suitable substituent(s) such as the above-mentioned lower alkyl, aryl [e.g. phenyl, naphthyl, etc.], the above-mentioned acyl, ar(lower)alkyl [e.g. benzyl, phenethyl, trityl, etc.], cycloalkyl [e.g. cyclopropyl, cyclobutyl, cyclopentyl, cyclohexyl, cycloheptyl, cyclooctyl, adamantyl, etc.], a heterocyclic group mentioned below, heterocyclic(lower)alkyl [e.g. pyridylmethyl, pyridylethyl, imidazolylmethyl, furylmethyl, thienylmethyl, morpholinomethyl, piperidinomethyl, etc.], substituted or unsubstituted amidino [e.g. amidino, methylamidino, N-ethyl-N'-cyanoamidino, etc.], or the like.

More preferable "amino acid residue" is a group of the formula:

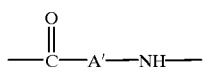

wherein A' is lower alkylene, most preferably, methylene.

Partial structures of the following formulas in the compounds [Ia] and [Ib]:

and

wherein $R^7$ and (AA) are each as defined above, are also included within "acyl".

Suitable aryl moiety such as in the terms "ar(lower)alkenoyl", "arylcarbamoyl", etc., may be phenyl, naphthyl, phenyl or naphthyl substituted with lower alkyl [e.g. tolyl, xylyl, mesityl, cumenyl, di(tert-butyl)phenyl, methylnaphthyl, etc.] and the like, in which preferable one is phenyl, naphthyl and tolyl.

Suitable "heterocyclic group" and heterocyclic moiety such as in the terms "heterocyclic(lower)alkanoyl", "heterocyclic(lower)alkenoyl", etc., may be saturated or unsaturated, monocyclic or polycyclic heterocyclic group containing at least one hetero-atom such as an oxygen, sulfur and/or nitrogen atom such as:

unsaturated 3 to 8-membered, preferably 5 or 6-membered heteromonocyclic group containing 1 to 4 nitrogen atom(s), for example, pyrrolyl, pyrrolinyl, imidazolyl, pyrazolyl, pyridyl, and its N-oxide, pyrimidinyl, pyrazinyl, pyridazinyl, triazolyl, tetrazolyl, dihydrotriazinyl, etc.;

saturated 3 to 8-membered, preferably 4 or 6-membered heteromonocyclic group containing 1 to 4 nitrogen atom(s), for example, azetidinyl, pyrrolidinyl, imidazolidinyl, piperidyl, pyrazolidinyl, piperazinyl, etc.;

unsaturated condensed 7 to 12-membered heterocyclic group containing 1 to 5 nitrogen atom(s), for example, indolyl, isoindolyl, indolizinyl, benzimidazolyl, quinolyl, isoquinolyl, tetrahydroquinolyl, indazolyl, benzotriazolyl, imidazopyridyl, etc.;

unsaturated 3 to 8-membered, preferably 5 or 6-membered heteromonocyclic group containing an oxygen atom, for example, furyl, etc.;

unsaturated condensed 7 to 12-membered heterocyclic group containing 1 to 2 oxygen atom(s), for example, benzofuryl, piperonyl, etc.;

unsaturated 3 to 8-membered, preferably 5 or 6-membered heteromonocyclic group containing a sulfur atom, for example, thienyl, etc.;

unsaturated condensed 7 to 12-membered heterocyclic group containing 1 to 2 sulfur atom(s), for example, benzothienyl, etc.;

unsaturated 3 to 8-membered, preferably 5 or 6-membered heteromonocyclic group containing 1 to 2 oxygen atom(s) and 1 to 3 nitrogen atom(s), for example, oxazolyl, isoxazolyl, oxadiazolyi, etc.;

saturated 3 to 8-membered, preferably 5 or 6-membered heteromonocyclic group containing 1 to 2 oxygen atom(s) and 1 to 3 nitrogen atom(s), for example, morpholinyl, etc.;

unsaturated condensed 7 to 12-membered heterocyclic group containing 1 to 2 oxygen atom(s) and 1 to 3 nitrogen atom(s), for example, benzoxazolyl, benzoxadiazolyl, etc.;

unsaturated 3 to 8-membered, preferably 5 or 6-membered heteromonocyclic group containing 1 to 2 sulfur atom(s) and 1 to 3 nitrogen atom(s), for example, thiazolyl, isothiazolyl, thiazolinyl, thiadiazolyl, etc.;

saturated 3 to 8-membered, preferably 5 or 6-membered heteromonocyclic group containing 1 to 2 sulfur atom(s) and 1 to 3 nitrogen atom(s), for example, thiazolidinyl, etc.;

unsaturated condensed 7 to 12-membered heterocyclic group containing 1 to 2 sulfur atom(s) and 1 to 3 nitrogen atom(s), for example, benzothiazolyl, benzothiadiazolyl, benzothiazinyl, benzothiazolinyl, etc., or the like.

Suitable "lower alkylene" may be a straight or branched one such as methylene, ethylene, trimethylene, methylmethylene, tetramethylene, ethylethylene, propylene, pentamethylene, hexamethylene or the like, in which the most preferable one is methylene.

Suitable "a leaving group" may be a conventional acid residue such as halogen [e.g. fluoro, chloro, bromo and iodo], arenesulfonyloxy [e.g. benzenesulfonyloxy, tosyloxy, etc.], alkanesulfonyloxy [e.g. mesyloxy, ethanesulfonyloxy, etc.], and the like.

Suitable pharmaceutically acceptable salts of the object compound [I] are conventional non-toxic salts and include a metal salt such as an alkali metal salt [e.g. sodium salt, potassium salt, etc.) and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], an organic acid addition salt (e.g. formate, acetate, trifluoroacetate, maleate, tartrate, oxalate, methanesulfonate, benzenesulfonate, toluenesulfonate, etc.], an inorganic acid addition salt [e.g. hydrochloride, hydrobromide, sulfate, phosphate, etc.], a salt with an amino acid [e.g. arginine salt, aspartic acid salt, glutamic acid salt, etc.], an intramolecular salt and the like.

With respect to the salts of the compounds [Ia] and [Ib] in the Process 2, it is to be noted that these compounds are included within the scope of the compound [I], and accordingly the suitable examples of the salts of these compounds are to be referred to those as exemplified for the object compound [I].

Preferred embodiments of the object compound [I] are as follows:
wherein
$R^1$ is lower alkyl,
$R^2$ is hydrogen, lower alkyl or a heterocyclic group [more preferably, unsaturated 5 or 6-membered heteromonocyclic group containing 1 to 4 nitrogen atom(s) (most preferably, pyrrolyl, imidazolyl, pyrazolyl, pyridyl, triazolyl, tetrazolyl, etc.), etc.],
$R^3$ is hydrogen, lower alkyl or halogen,
$R^4$ is lower alkyl or halogen,
$R^5$ is nitro or a group of the formula:

wherein
$R^6$ is hydrogen or lower alkyl,
$R^8$ is acyl [more preferably, lower alkanoyl or a group of the formula:

—(AA)—$R^7$, etc.

in which $R^7$ is lower alkanoyl; lower alkylsulfonyl; aroyl (more preferably, benzoyl, etc.); heterocycliccarbonyl (more preferably, pyridylcarbonyl, etc.); ar(lower)alkenoyl substituted with a substituent selected from the group consisting of acyl and acylamino (more preferably, cinnamoyl substituted with a substituent selected from the group consisting of lower alkylcarbamoyl, pyridyl(lower)alkylcarbamoyl, pyridylcarbamoyl, lower alkanoylamino, pyridyl(lower)alkanoylamino and pyridylcarbonylamino); heterocyclic(lower)alkenoyl substituted with a substituent selected from the group consisting of acyl and acylamino (more preferably, pyridylacryloyl substituted with a substituent selected from the group consisting of lower alkylcarbamoyl, pyridyl(lower)alkylcarbamoyl, pyridylcarbamoyl, lower alkanoylamino, pyridyl(lower)alkanoylamino and pyridylcarbonylamino); or arylcarbamoyl substituted with a substituent selected from the group consisting of acyl and acylamino (more preferably, phenylcarbamoyl substituted with a substituent selected from the group consisting of lower alkylcarbamoyl, pyridyl(lower)alkylcarbamoyl, pyridylcarbamoyl, lower alkanoylamino, pyridyl(lower)alkanoylamino and pyridylcarbonylamino); and (AA) is amino acid residue (most preferably, glycyl); and A is lower alkylene [most preferably, methylene].

The processes for preparing the object compound [I] are explained in detail in the following.

Process 1

The object compound [I] or its salt can be prepared by reacting a compound [II] or its salt with a compound [III] or its salt.

Suitable salts of the compounds [II] and [III] may be the same as those exemplified for the compound [I].

The reaction is preferably carried out in the presence of a base such as alkali metal [e.g. lithium, sodium, potassium, etc.], the hydroxide or carbonate or bicarbonate thereof [e.g. sodium hydroxide, potassium carbonate, potassium bicarbonate, etc.], alkali metal alkoxide [e.g. sodium methoxide, sodium ethoxide, potassium tert-butoxide, etc.], or the like.

This reaction is usually carried out in a conventional solvent such as tetrahydrofuran, dioxane, N,N-dimethylformamide, acetone, or the like.

The reaction temperature is not critical, and the reaction is usually carried out under cooling to heating.

Process 2

The object compound [Ib] or its salt can be prepared by acylating a compound [Ia] or its salt.

The acylation is carried out in the presence of an acylating agent.

Suitable acylating agents are the corresponding carboxylic acid or sulfonic acid compounds, which are represented by the formula: $R^7$—OH wherein $R^7$ is as defined above, and reactive derivatives thereof, and the corresponding isocyanate or isothiocyanate compounds.

As suitable said reactive derivatives, there may be mentioned acid halides, acid anhydrides, active amides and active esters. Suitable examples are acid halides such as acid chloride and acid bromide, mixed acid anhydrides with various acids [e.g. substituted phosphoric acid such as dialkyl phosphoric acid, sulfuric acid, aliphatic carboxylic acid, aromatic carboxylic acid, etc.], symmetric acid anhydrides, active amides with various imidazoles, and active esters such as p-nitrophenyl ester and N-hydroxysuccinimide ester. The kind of such reactive derivatives can be selected depending on the kind of acyl group to be introduced.

The reaction is usually carried out in a conventional solvent, such as methylene chloride, chloroform, pyridine, dioxane, tetrahydrofuran, N,N-dimethylformamide, or the like. In case that the acylating agent is liquid, it can also be used as a solvent. In case that the carboxylic acid or sulfonic acid compounds are used as acylating agent in the free acid form or salt form, it is preferable to carry out the reaction in the presence of a conventional condensing agent such as 1-ethyl-3-(3-dimethylaminopropyl)carbodiimide, N,N'-dicyclohexylcarboxiimide or the like.

The reaction temperature is not critical and the reaction can be carried out under cooling, at ambient temperature, or under heating.

This reaction is preferably carried out in the presence of a conventional inorganic base or in the presence of a conventional organic base.

The object compound [I] and the starting compounds can also be prepared by the methods of Examples mentioned below or similar manners thereto or conventional manners.

The compounds obtained by the above processes can be isolated and purified by a conventional method such as pulverization, recrystallization, chromatography, reprecipitation or the like.

It is to be noted that the compound [I] and the other compounds may include one or more stereoisomers and geometrical isomers due to asymmetric carbon atoms and double bonds, and all of such isomers and mixture thereof are included within the scop of this invention.

The compound of the formula [I] and its salt can be in the form of a solvate, which is included within the scope of the present invention. The solvate preferably includes a hydrate and an ethanolate.

The object compound [I] and pharmaceutically acceptable salts thereof possess strong activities as bradykinin antagonists, and are useful for the treatment and/or the prevention of bradykinin or its analogues mediated diseases such as allergy, inflammation, autoimmune disease, shock, pain, or the like, and more particularly for the prevention and/or the treatment of asthma, cough, bronchitis, rhinitis, rhinorrhea, obstructive pulmonary disease [e.g. pulmonary emphysema, etc.], expectoration, pneumonitis, systemic inflammatory response syndrome (SIRS), septic shock, endotoxin shock, anaphylactic shock, adult respiratory distress syndrome, disseminated intravascular coagulopathy, arthritis, rheumatism, osteoarthritis, lumbago, inflammation-induced bone resorption, conjunctivitis, vernal conjunctivitis, uveitis, iritis, iridocyclitis, headache, migraine, toothache, backache, superficial pain, cancerous pain, postoperative pain, tenalgia, trauma [e.g. wound, burn, etc.], rash, erythema, eczema or dermatitis [e.g. contact dermatitis, atopic dermatitis, etc.], urticaria, herpes, itching, psoriasis, lichen, inflammatory bowel disease [e.g. ulcerative colitis, Crohn's disease, etc.], diarrhea, emesis, hepatitis, pancreatitis, gastritis, esophagitis, food allergy, ulcer, irritable bowel syndrome, nephritis, angina, periodontitis, edema, hereditary angioneurotic edema, cerebral edema (traumatic cerebral edema), cerebral infarction, low blood pressure, thrombosis, myocardial infarction, cerebral vasospasm, congestion, coagulation, gout, central nervous system injury, premature labor, arteriosclerosis (hyperlipidemia, hypercholesterolemia), postgastrectomy dumping syndrome, carcinoid syndrome, altered sperm mobility, diabetic neuropathy, neuralgia, graft rejection in transplantation, or the like, in human being or animals.

And further, it is known that bradykinin relates to the release of mediators such as prostaglandins, leukotrienes, tachykinins, histamine, thromboxanes, or the like, so the compound [I] is expected to be useful for the prevention and/or the treatment of such mediators mediated diseases.

In order to illustrate the usefulness of the object compound [I], the pharmacological test data of some representative compounds of the compound [I] are shown in the following.

$^3$H-Bradykinin Receptor Binding (i) Test Method (a) Crude Ileum Membrane Preparation Male Hartly strain guinea pigs were sacrificed by decapitation. The ileum was removed and homogenized in buffer (50 mM 2-[[tris(hydroxymethyl)methyl]amino]-1-ethanesulfonic acid (TES), 1 mM 1,10-phenanthroline pH 6.8). The homogenate was centrifuged (1000×g, 20 minutes) to remove tissue clumps and the supernatant was centrifuges (100,000×g, 60 minutes) to yield a pellet. The pellet was resuspended in buffer (50 mM TES, 1 mM 1,10-phenanthroline, 140 mg/l bacitracin, 1 mM dithiothreiol, 0.1% bovine serum albumin pH 6.8) and homogenized with a glass-teflon homogenizer to yield suspension which was referred to as crude membrane suspension. The obtained membrane suspension was stored at −80° C. until use.

(b) $^3$H-Bradykinin Binding to the Membrane

The frozen crude membrane suspension was thawed. In binding assays, $^3$H-Bradykinin (0.06 nM) and drug were incubated with 50 μl of the membrane suspension at room temperature for 60 minutes in a final volume of 250 μl. Separation of receptor-bound from free $^3$H-Bradykinin is achieved by immediate filtration under vacuum and washed three times with 5 ml of ice-cold buffer (50 mM Tris-HCl pH 7.5). Non-specific binding was defined as binding in the presence of 0.1 μM Bradykinin. The radioactivity retained on rinsed filters was determined by a liquid-scintillation counter.

(ii) Test Results

| Test Compound (Example No.) | Inhibition of $^3$H-Bradykinin binding IC$_{50}$ (M) |
|---|---|
| 2-(3) (trihydrochloride) | 4.5 × 10$^{-9}$ |
| 3 (trihydrochloride) | 6.6 × 10$^{-9}$ |
| 11-(4) (dihydrochloride) | 3.3 × 10$^{-9}$ |
| 12 (dihydrochloride) | 9.1 × 10$^{-9}$ |
| 17-(1) | 3.9 × 10$^{-9}$ |

The effects of the compound [I] on bradykinin-induced bronchoconstriction and carrageenin-induced paw edema were measured according to similar manners described in British Journal of Pharmacology, 102, 774–777 (1991).

For therapeutic purpose, the compound [I] and a pharmaceutically acceptable salt thereof of the present invention can be used in a form of pharmaceutical preparation containing one of said compounds, as an active ingredient, in admixture with a pharmaceutically acceptable carrier such as an organic or inorganic solid, semi-solid or liquid excipient suitable for oral, parenteral such as intravenous, intramuscular, subcutaneous or intraarticular, external such as topical, enteral, intrarectal, transvaginal, inhalant, ophthalmic, nasal of hypoglossal administration. The pharmaceutical preparations may be capsules, tablets, dragees, granules, suppositories, solution, lotion, suspension, emulsion, ointment, gel, cream, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for preventing and/or treating the above-mentioned diseases. In general, amounts between 0.1 mg/body and about 1,000 mg/body may be administered per day.

EXAMPLES

The following Examples are given for the purpose of illustrating this invention.

Example 1

(1) The solution of 4-chloro-8-hydroxy-2-methylquinoline (2.0 g), imidazole (3.52 g) in dioxane (20 ml) was refluxed for 18 hours. The cooled reaction mixture was added chloroform and aqueous sodium bicarbonate solution. The organic layer was washed with water and dried over magnesium sulfate and evaporated in vacuo. The residue was crystallized from ether to give 8-hydroxy-4-(imidazol-1-yl)-2-methylquinoline (1.99 g) as colorless crystals.

mp: 192–196° C.

NMR (CDCl$_3$, δ): 2.79 (3H, s), 7.20–7.37 (5H, m), 7.45 (1H, t, J=7.5 Hz), 7.86 (1H, s).

(2) To a mixture of 2,6-dichloro-1-mesyloxymethyl-3-(N-methyl-N-phthalimidoacetylamino)benzene (2.35 g), tetrabutylammonium iodide (123 mg) and molecular sieves 4A (340 mg) in N,N-dimethylformamide (38 ml) were added 8-hydroxy-4-(imidazol-1-yl)-2-methylquinoline (750 mg) and potassium carbonate (2.3 g) under ice-cooling, and the mixture was stirred for 15 minutes at the same temperature and overnight at ambient temperature. Water and chloroform were added thereto, and the separated organic layer was washed with water and brine, dried over magnesium sulfate and evaporated in vacuo. The residue was crystallized with ethyl acetate to give 8-[2,6-dichloro-3-(N-phthalimidoacetyl-N-methylamino)benzyloxy]-4-(imidazol-1-yl)-2-methylquinoline (1.92 g) as colorless crystals.

mp: 200–203° C.

NMR (CDCl$_3$, δ): 2.81 (3H, s), 3.25 (3H, s), 4.09 (2H, s), 5.70 (1H, d, J=10 Hz), 5.77 (1H, d, J=10 Hz), 7.24–7.64 (8H, m), 7.69–7.78 (2H, m), 7.81–7.90 (3H, m).

(3) To a suspension of 8-[2,6-dichloro-3-(N-phthalimidoacetyl-N-methylamino)benzyloxy]-4-(imidazol-1-yl)-2-methylquinoline (1.91 g) in ethanol (19 ml) was added hydrazine monohydrate (318 mg), and the mixture was refluxed for 1 hour. After cooling, the resulting precipitates was filtered off. The filtrate was concentrated in vacuo, and the residue was dissolved in chloroform. Insoluble material was filtered off, and the filtrate was concentrated in vacuo. The residue was pulverized with diisopropyl ether to give 8-[3-(N-glycyl-N-methylamino)-2,6-dichlorobenzyloxy]-4-(imidazol-1-yl)-2-methylquinoline (1.5 g) as colorless amorphous.

NMR (CDCl$_3$, δ): 2.70 (3H, br s), 2.92–3.12 (2H, m), 3.24 (3H, br s), 5.68 (2H, br s), 7.18–7.55 (8H, m), 7.85 (1H, br s).

(4) To a solution of 8-[3-(N-glycyl-N-methylamino)-2,6-dichlorobenzyloxy]-4-(imidazol-1-yl)-2-methylquinoline (80 mg), 4-(dimethylcarbamoyl)cinnamic acid (41 mg) and 1-hydroxybenzotriazole (29.9 mg) in dichloromethane (0.8 ml) was added 1-ethyl-3-(3-dimethylaminopropyl) carbodiimide hydrochloride (39.1 mg) at ambient temperature, and the mixture was stirred for 3 hours at the same temperature. To the mixture was added saturated sodium bicarbonate solution, and the separated organic layer was dried over magnesium sulfate and evaporated in vacuo. The residue was purified by preparative thin layer chromatography (chloroform:methanol, 10:1, v/v) to give 8-[2,6-dichloro-3-[N-[4-(dimethylcarbamoyl)cinnamoylglycyl]-N-methylamino]benzyloxy]-4-(imidazol-1-yl)-2-methylquinoline (104 mg) as colorless amorphous.

NMR (CDCl$_3$, δ): 2.80 (3H, s), 2.99 (3H, br s), 3.12 (3H, br s), 3.29 (3H, s), 3.70 (1H, dd, J=17, 4 Hz), 3.91 (1H, dd, J=17, 5 Hz), 5.67 (2H, s), 6.51 (1H, d, J=15 Hz), 6.66 (1H, br t, J=5 Hz), 7.26–7.62 (13H, m) , 7.84 (1H, s).

its dihydrochloride

NMR (DMSO-d$_6$, δ): 2.71 (3H, s), 2.92 (3H, br s), 2.98 (3H, br s), 3.17 (3H, s), 3.22–4.10 (2H, overlapped with H$_2$O), 5.52 (1H, d, J=10 Hz), 5.61 (1H, d, J=10 Hz), 6.87 (1H, d, J=15 Hz), 7.28 (1H, d, J=7.5 Hz), 7.28–7.47 (3H, m), 7.48–7.70 (4H, m), 7.41–7.86 (3H, m), 8.05 (1H, s), 8.25 (1H, s), 8.38 (1H, br t, J=5 Hz), 9.66 (1H, s).

Example 2

The following compounds were obtained according to a similar manner to that of Example 1-(4).

(1) 8-[2,6-Dichloro-3-[N-methyl-N-[4-(4-pyridylcarbamoyl)cinnamoylglycyl]amino]benzyloxy]-4-(imidazol-1-yl)-2-methylquinoline NMR (CDCl$_3$, δ): 2.75 (3H, s), 3.26 (3H, s), 3.63 (1H, dd, J=17, 4 Hz), 3.90 (1H, dd, J=17, 5 Hz), 5.65 (2H, s), 6.53 (1H, d, J=15 Hz), 6.73 (1H, br s), 7.28–7.33 (3H, m), 7.38 (1H, br d, J=8 Hz), 7.40–7.60 (6H, m), 7.63 (2H, d, J=7 Hz), 7.81–7.91 (3H, m), 8.44 (1H, s), 8.53 (2H, d, J=7 Hz).

its trihydrochloride

NMR (CDCl$_3$—CD$_3$OD, δ): 3.13 (3H, br s), 3.29 (3H, s), 3.83 (1H, br d, J=17 Hz), 3.99 (1H, br d, J=17 Hz), 5.68 (1H, br d, J=10 Hz), 5.79 (1H, br d, J=10 Hz), 6.64 (1H, br d, J=15 Hz), 7.40 (1H, br d, J=15 Hz), 7.50–7.65 (6H, m), 7.72 (1H, br d, J=8 Hz), 7.82 (1H, br S), 7.93 (1H, br s), 8.02 (2H, br d, J=7 Hz), 8.18 (1H, br s), 8.33 (1H, br s), 8.55 (4H, br s).

(2) 8-[2,6-Dichloro-3-[N-methyl-N-[4-(4-pyridinecarboxamido)cinnamoylglycyl]amino]benzyloxy]-4-(imidazol-1-yl)-2-methylquinoline NMR (CDCl$_3$, δ): 2.75 (3H, s), 3.25 (3H, s), 3.60 (1H, dd, J=17, 4 Hz), 3.64 (1H, dd, J=17, 4 Hz), 3.90 (1H, dd, J=17, 5 Hz), 5.65 (2H, s), 6.42 (1H, d, J=15 Hz), 6.63 (1H, br d, J=5 Hz), 7.26–7.62 (10H, m), 7.65–7.76 (5H, m), 7.84 (1H, s), 8.44 (1H, s), 8.76 (2H, d, J=8 Hz).

its trihydrochloride

NMR (DMSO-d$_6$, δ): 2.72 (3H, s), 3.17 (3H, s), 3.33–4.50 (2H, overlapped with H$_2$O), 5.53 (1H, d, J=10 Hz), 5.59 (1H, d, J=10 Hz), 6.77 (1H, d, J=15 Hz), 7.31 (1H, br d, J=8 Hz), 7.38 (1H, d, J=15 Hz), 7.59–7.80 (4H, m), 7.82–7.91 (4H, m), 8.05 (1H, s), 8.14 (2H, d, J=8 Hz), 8.25 (1H, s), 8.30 (1H, br t, J=5 Hz), 8.93 (2H, d, J=8 Hz), 9.67 (1H, s), 10.95 (1H, s).

(3) 8-[2,6-Dichloro-3-[N-methyl-N-[4-[N-(2-pyridylmethyl)carbamoyl]cinnamoylglycyl]amino]benzyloxy]-4-(imidazol-1-yl)-2-methylquinoline NMR (CDCl$_3$, δ): 2.80 (3H, s), 3.29 (3H, s), 3.68 (1H, dd, J=17, 4 Hz), 3.94 (1H, dd, J=17, 4 Hz), 4.78 (2H, d, J=5 Hz), 5.65 (1H, d, J=10 Hz), 5.70 (1H, d, J=10 Hz), 6.55 (1H, d, J=15 Hz), 6.70 (1H, br s), 7.21–7.74 (15H, m), 7.81–7.92 (3H, m), 8.59 (1H, br d, J=5 Hz).

its trihydrochioride

NMR (CDCl$_3$—CD$_3$OD, δ): 3.04–3.12 (3H, overlapped with H$_2$O), 3.87 (1H, d, J=17, 4 Hz), 3.97 (1H, d, J=17 Hz), 4.99 (2H, s), 5.64 (1H, d, J=10 Hz), 5.76 (1H, d, J=10 Hz), 6.65 (1H, d, J=15 Hz), 7.43–7.64 (6H, m), 7.72 (1H, br d, J=8 Hz), 7.80–8.00 (6H, m), 8.16 (1H, br d, J=8 Hz), 8.28 (1H, br s), 8.38 (1H, br s), 8.46 (1H, br t, J=8 Hz), 8.72 (1H, br d, J=7 Hz).

Example 3

A mixture of 8-[3-(N-glycyl-N-methylamino)-2,6-dichlorobenzyloxy]-4-(imidazol-1-yl)-2-methyiquinoline (60 mg), phenyl 3-[N-(4-pyridyl)carbamoyl] phenylcarbamate (44.6 mg) and triethylamine (25.8 mg) in N,N-dimethylformamide (0.6 ml) was warmed at 80° C. for 2 hours. Water and ethyl acetate were added thereto, and the separated organic layer was washed with water, dried over magnesium sulfate and evaporated in vacuo. The residue was purified by preparative thin layer chromatography (chloroform:methanol, 10:1, v/v) to give 8-[2,6-dichloro-3-[N-methyl-N-[N'-[3-[N-(4-pyridyl)carbamoyl]phenyl]ureidoacetyl]amino]benzyloxy]-4-(imidazol-1-yl)-2-methylquinoline (57 mg) as colorless amorphous.

NMR (CDCl$_3$, δ): 2.76 (3H, s), 3.27 (3H, s), 3.91–4.01 (2H, m), 5.39 (1H, br d, J=10 Hz), 5.54 (1H, d, J=10 Hz), 6.50 (1H, br s), 6.90 (1H, s), 7.04 (1H, t, J=8 Hz), 7.23–7.58 (10H, m), 7.48 (1H, s), 7.90 (2H, br d, J=7 Hz), 8.31 (1H, br s), 8.52 (2H, br d, J=7 Hz), 9.64 (1H, br s).

its trihydrochloride

NMR (CDCl$_3$—CD$_3$OD, δ): 3.07 (3H, br s), 3.17–3.32 (3H, overlapped with H$_2$O), 3.80–3.89 (2H, m), 5.67 (1H, br d, J=10 Hz), 5.80 (1H, br d, J=10 Hz), 7.26 (1H, br s), 7.45 (1H, br s), 7.53–7.65 (4H, m), 7.72 (1H, br s), 7.82 (2H, br s), 7.93 (1H, br s), 8.19 (1H, br s), 8.34–8.51 (6H, m).

Example 4

To a stirred solution of 8-[3-(N-glycyl-N-methylamino)-2,6-dichlorobenzyloxy]-4-(imidazol-1-yl)-2-methylquinoline (60 mg) in dichloromethane (0.6 ml) were added acetic anhydride (15.6 mg) and pyridine (15.1 mg) at ambient temperature, and the mixture was stirred for 3 hours at the same temperature. The mixture was concentrated in vacuo, and the residue was purified by preparative thin layer chromatography (chloroform:methanol, 10:1, v/v) to give 8-[3-(N-(acetylglycyl)-N-methylamino]-2,6-dichlorobenzyloxy]-4-(imidazol-1-yl)-2-methylquinoline (53 mg) as colorless amorphous.

NMR (CDCl$_3$, δ): 2.00 (3H, s), 2.80 (3H, s), 3.25 (3H, s), 3.50 (1H, dd, J=17, 4 Hz), 3.80 (1H, dd, J=17, 5 Hz), 5.66 (2H, br s), 6.42 (1H, br s), 7.28–7.52 (8H, m), 7.82 (1H, br s).

Example 5

To a stirred solution of 8-[3-(N-glycyl-N-methylamino)-2,6-dichlorobenzyloxy]-4-(imidazol-1-yl)-2-methylquinoline (80 mg) and triethylamine (22.4 mg) in dichloromethane (1 ml) was dropwise added isobutyryl chloride (19.9 mg) under ice-cooling, and the mixture was stirred for 15 minutes at the same temperature and for 2 hours at ambient temperature. The mixture was washed with saturated sodium bicarbonate solution, water and brine, dried over magnesium sulfate and evaporated in vacuo. The residue was purified by preparative thin layer chromatography (chloroform:methanol, 10:1, v/v) to give 8-[3-[N-(isobutyrylglycyl)-N-methylamino]-2,6-dichlorobenzyloxy]-4-(imidazol-1-yl)-2-methylquinoline (69 mg) as colorless amorphous.

NMR (CDCl$_3$, δ): 1.14 (6H, d, J=7 Hz), 2.41 (1H, m), 2.80 (3H, s), 3.25 (3H, s), 3.47 (1H, dd, J=17, 4 Hz), 3.81 (1H, dd, J=17, 5 Hz), 5.65 (2H, br s), 6.41 (1H, br s), 7.28–7.51 (8H, m), 7.83 (1H, br s).

Example 6

The following compounds were obtained according to a similar manner to that of Example 5.

(1) 8-[3-[N-(Benzoylglycyl)-N-methylamino]-2,6-dichlorobenzyloxy]-4-(imidazol-1-yl)-2-methylquinoline NMR (CDCl$_3$, δ): 2.80 (3H, s), 3.29 (3H, s), 3.69 (1H, dd, J=17, 4 Hz), 4.00 (1H, dd, J=17, 5 Hz), 5.64 (1H, d, J=10 Hz), 5.70 (1H, d, J=10 Hz), 7.12 (1H, br t, J=5 Hz), 7.28–7.54 (11H, m), 7.75–7.85 (3H, m).

(2) 8-[2,6-Dichloro-3-[N-methyl-N-(propionylglycyl) amino]benzyloxy]-2-methyl-4-(imidazol-1-yl)quinoline NMR (CDCl$_3$, δ): 1.15 (3H, t, J=7.5 Hz), 2.24 (2H, q, J=7.5 Hz), 2.80 (3H, s), 3.25 (3H, s), 3.49 (1H, dd, J=4, 16 Hz), 3.81 (1H, dd, J=4, 16 Hz), 5.60–5.70 (2H, m), 6.41 (1H, br peak), 7.21–7.54 (8H, m), 7.83 (1H, s).

(3) 8-[2,6-Dichloro-3-[N-methyl-N-(isonicotinoylglycyl)-amino]benzyloxy]-2-methyl-4-(imidazol-1-yl)quinoline NMR (CDCl$_3$, δ): 2.80 (3H, s), 3.30 (3H, s), 3.72 (1H, dd, J=4, 16 Hz), 3.98 (1H, dd, J=4, 16 Hz), 5.67 (1H, s-like), 7.21–7.59 (9H, m), 7.64 (2H, d, J=6 Hz), 7.84 (1H, s), 8.75 (2H, d, J=6 Hz).

Example 7

To a stirred solution of 8-[3-(N-glycyl-N-methylamino)-2,6-dichlorobenzyloxy]-4-(imidazol-1-yl)-2-methylquinoline (80 mg) and triethylamine (22.4 mg) in dichloromethane (1 ml) was dropwise added mesyl chloride (21.4 mg) under ice-cooling, and the mixture was stirred for 15 minutes at the same temperature and for 2 hours at ambient temperature. The mixture was washed with saturated sodium bicarbonate solution, water and brine, dried over magnesium sulfate and evaporated in vacuo. The residue was purified by preparative thin layer chromatography (chloroform:methanol, 10:1, v/v) to give 8-[2,6-dichloro-3-[N-(mesylglycyl)-N-methylamino]benzyloxy]-4-(imidazol-1-yl)-2-methylquinoline (70 mg) as colorless amorphous.

NMR (CDCl$_3$, δ): 2.80 (3H, s), 2.95 (3H, s), 3.28 (3H, s), 3.50 (1H, dd, J=17, 5 Hz), 3.67 (1H, dd, J=17, 5 Hz), 5.16 (1H, br t, J=5 Hz), 5.64 (1H, d, J=10 Hz), 5.70 (1H, d, J=10 Hz), 7.24–7.57 (8H, m), 7.83 (1H, br s).

Example 8

A suspension of 8-hydroxy-4-(imidazol-1-yl)-2-methylquinoline (23 mg), 2,6-dichloro-3-[N-methyl-N-[4-(methylcarbamoyl)cinnamoylglycyl]amino]benzyl bromide (52.4 mg) and potassium carbonate (42.3 mg) in N,N-dimethylformamide (0.5 ml) was stirred for 3 hours at ambient temperature. Water was added thereto, and the resulting precipitate was collected by filtration. The residue was purified by preparative thin layer chromatography (chloroform:methanol, 10:1, v/v) to give 8-[2,6-dichloro-3-[N-methyl-N-[4-(methylcarbamoyl)cinnamoylglycyl] amino]benzyloxy]-4-(imidazol-1-yl)-2-methylquinoline (60 mg) as colorless amorphous.

NMR (CDCl$_3$, δ): 2.79 (3H, s), 3.02 (3H, d, J=5 Hz), 3.29 (3H, s), 3.67 (1H, dd, J=17, 4 Hz), 3.93 (1H, dd, J=17, 5 Hz), 5.64 (1H, d, J=10 Hz), 5.69 (1H, d, J=10 Hz), 6.20 (1H, br d, J=5 Hz), 6.52 (1H, d, J=15 Hz), 6.68 (1H, br t, J=5 Hz), 7.30–7.61 (10H, m), 7.75 (2H, br d, J=7.5 Hz), 7.83 (1H, s).

its dihydrochloride

NMR (CDCl$_3$—CD$_3$OD, δ): 2.97 (3H, s), 3.10 (3H, s), 3.29 (3H, s), 3.81 (1H, d, J=17 Hz), 3.93 (1H, d, J=17 Hz), 5.64 (1H, d, J=10 Hz), 5.76 (1H, d, J=10 Hz), 6.60 (1H, br d, J=15 Hz), 7.42–7.96 (12H, m), 8.18 (1H, br s), 8.30 (1H, br s).

Example 9

(1) 8-Hydroxy-2-methyl-4-(pyrazol-1-yl)quinoline was obtained by reacting 4-chloro-8-hydroxy-2-methylquinoline with pyrazole according to a similar manner to that of Example 1-(1).

mp: 53–54° C.

NMR (CDCl$_3$, δ): 2.78 (3H, s), 6.60 (1H, d, J=3 Hz), 7.20 (1H, d, J=8 Hz), 7.44 (1H, t, J=8 Hz), 7.46 (1H, s), 7.64 (1H, d, J=8 Hz), 7.79 (1H, br s), 7.98 (1H, d, J=3 Hz).

(2) 8-[2,6-Dichloro-3-[N-methyl-N-[4-(methylcarbamoyl)cinnamoylglycyl]amino]benzyloxy]-2-methyl-4-(pyrazol-1-yl)quinoline was obtained according to a similar manner to that of Example 8.

NMR (CDCl$_3$, δ): 2.78 (3H, s), 3.02 (3H, d, J=5 Hz), 3.26 (3H, s), 3.59 (1H, dd, J=17, 4 Hz), 3.92 (1H, dd, J=17, 5 Hz), 5.68 (2H, s), 6.24 (1H, br d, J=5 Hz), 6.52 (1H, d, J=15 Hz), 6.59 (1H, br s), 6.70 (1H, br t, J=5 Hz), 7.30–7.38 (2H, m), 7.39 (1H, s), 7.43–7.61 (5H, m), 7.71–7.80 (3H, m), 7.90 (2H, d, J=8 Hz), 7.88 (1H, br s), 7.91 (1H, br s).

its dihydrochloride

NMR (CDCl$_3$—CD$_3$OD, δ): 2.95 (3H, s), 3.12 (3H, s), 3.27 (3H, s), 3.87 (1H, d, J=17 Hz), 4.09 (1H, d, J=17 Hz), 5.58 (1H, d, J=10 Hz), 5.69 (1H, d, J=10 Hz), 6.61 (1H, d, J=15 Hz), 6.75 (1H, br s), 7.38 (1H, d, J=15 Hz), 7.44–7.55 (4H, m), 7.62 (1H, d, J=8 Hz), 7.71 (2H, d, J=8 Hz), 7.85 (1H, t, J=8 Hz), 8.01 (1H, br s), 8.11 (1H, br s), 8.55 (1H, br s), 8.62 (1H, d, J=8 Hz).

Example 10

(1) 8-Hydroxy-2-methyl-4-(1,2,4-triazol-1-yl)quinoline was obtained by reacting 4-chloro-8-hydroxy-2-methylquinoline with 1,2,4-triazole according to a similar manner to that of Example 1-(1).

mp: 152–154° C.

NMR (CDCl$_3$, δ): 2.80 (3H, s), 7.21–7.28 (1H, overlapped with CDCl$_3$), 7.40–7.54 (3H, m), 8.27 (1H, s), 8.35 (1H, br s), 8.60 (1H, s).

(2) 8-[2,6-Dichloro-3-[N-methyl-N-[4-(methylcarbamoyl)cinnamoylglycyl]amino]benzyloxy]-2-methyl-4-(1,2,4-triazol-1-yl)quinoline was obtained according to a similar manner to that of Example 8.

NMR (CDCl$_3$, δ): 2.81 (3H, s), 3.02 (3H, d, J=5 Hz), 3.29 (3H, s), 3.62 (1H, dd, J=17, 4 Hz), 3.92 (1H, dd, J=17, 5 Hz), 5.69 (2H, s), 6.19 (1H, br d, J=5 Hz), 6.53 (1H, d, J=15 Hz), 6.67 (1H, br t, J=5 Hz), 7.30–7.42 (2H, m), 7.49–7.62 (6H, m), 7.76 (2H, d, J=8 Hz), 8.28 (1H, s), 8.58 (1H, s).

its dihydrochloride

NMR (CDCl$_3$—CD$_3$OD, δ): 2.95 (3H, s), 3.18 (3H, br s), 3.27 (3H, s), 3.87 (1H, d, J=17 Hz), 4.03 (1H, d, J=17 Hz), 5.60 (1H, d, J=10 Hz), 5.70 (1H, d, J=10 Hz), 6.60 (1H, d, J=15 Hz), 7.39 (1H, d, J=15 Hz), 7.44–7.60 (4H, m), 7.63–7.72 (3H, m), 7.89 (1H, t, J=8 Hz), 8.31–8.42 (3H, m), 9.43 (1H, br s).

Example 11

(1) 1-tert-Butyldiphenylsilyloxymethyl-2,6-dichloro-3-[N-methyl-N-[4-(dimethylcarbamoyl)cinnamoylglycyl]amino]benzene was obtained from 1-tert-butyldiphenylsilyloxymethyl-2,6-dichloro-3-(N-glycyl-N-methylamino)benzene and 4-(dimethylcarbamoyl)cinnamic acid according to a similar manner to that of Example 1-(4).

NMR (CDCl$_3$, δ): 1.05 (9H, s), 2.98 (3H, br s), 3.10 (3H, br s), 3.22 (3H, s), 3.56 (1H, dd, J=17, 4 Hz), 3.94 (1H, dd, J=17, 5 Hz), 4.91 (1H, d, J=10 Hz), 4.97 (1H, d, J=10 Hz), 6.49 (1H, d, J=15 Hz), 6.60 (1H, br s), 7.22 (1H, d, J=8 Hz), 7.34–7.60 (12H, m), 7.69–7.78 (4H, m).

(2) To a solution of 1-tert-butyldiphenylsilyloxymethyl-2,6-dichloro-3-[N-methyl-N-[4-(dimethylcarbamoyl)cinnamoylglycl]amino]benzene (3.0 g) in tetrahydrofuran (30 ml) was added 1M solution of tetrabutylammonium fluoride in tetrahydrofuran (6.4 ml) at ambient temperature, and the mixture was stirred for 1 hour at the same temperature. Water and ethyl acetate were added thereto, and the separated aqueous layer was extracted with chloroform. The combined organic layer was dried over magnesium sulfate and evaporated in vacuo. The residue was purified by flash chromatograpy on silica gel (chloroform-methanol) to give 2,6-dichloro-1-hydroxymethyl-3-[N-methyl-N-[4-(dimethylcarbamoyl)cinnamoylglycyl]amino]benzene (2.0 g) as colorless amorphous.

NMR (CDCl$_3$, δ): 2.99 (3H, br s), 3.12 (3H, br s), 3.26 (3H, s), 3.66 (1H, dd, J=17, 4 Hz), 3.90 (1H, dd, J=17, 5 Hz), 5.02 (2H, br s), 6.49 (1H, d, J=15 Hz), 6.64 (1H, br s), 7.28 (1H, d, J=8 Hz), 7.39–7.62 (6H, m).

(3) To a stirred solution of 2,6-dichloro-1-hydroxymethyl-3-[N-methyl-N-[4-(dimethylcarbamoyl)cinnamoylglycyl]amino]benzene (300 mg) and triethylamine (78.5 mg) in dichloromethane (3 ml) was dropwise added mesyl chloride (81.4 mg) under ice-cooling, and the mixture was stirred for 10 minutes at the same temperature and for 30 minutes at ambient temperature. Chloroform was added thereto, and the mixture was washed with saturated sodium bicarbonate solution, water and brine, dried over magnesium sulfate and evaporated in vacuo to give 2,6-dichloro-1-methanesulfonyloxymethyl-3-[N-methyl-N-[4-(dimethylcarbamoyl)cinnamoylglycyl]amino]benzene (330 mg) as colorless amorphous.

NMR (CDCl$_3$, δ): 2.98 (3H, br s), 3.15–3.16 (6H, m), 3.26 (3H, s), 3.62 (1H, dd, J=17, 4 Hz), 3.92 (1H, dd, J=17, 5 Hz), 5.54 (2H, br s), 6.49 (1H, d, J=15 Hz), 6.62 (1H, br s), 7.35–7.44 (3H, m), 7.48–7.61 (4H, m).

(4) 8-[2,6-Dichloro-3-[N-methyl-N-[4-(dimethylcarbamoyl)cinnamoylglycyl]amino]benzyloxy]-2-methyl-4-(pyrazol-1-yl)quinoline was obtained according to a similar manner to that of Example 1-(2).

NMR (CDCl$_3$, δ): 2.79 (3H, s), 2.98 (3H, br s), 3.11 (3H, br s), 3.28 (3H, s), 3.58 (1H, dd, J=17, 4 Hz), 3.92 (1H, dd, J=17, 5 Hz), 5.68 (2H, s), 6.50 (1H, d, J=15 Hz), 6.58 (1H, br s), 6.67 (1H, br s), 7.32 (2H, d, J=8 Hz), 7.38–7.61 (8H, m), 7.78 (1H, br d, J=8 Hz), 7.84 (1H, s).

its dihydrochloride

NMR (CDCl$_3$—CD$_3$OD, δ): 3.05 (6H, br s), 3.12 (3H, br s), 3.30 (3H, s), 3.92 (1H, br d, J=17 Hz), 4.07 (1H, br d, J=17 Hz), 5.63 (1H, br d, J=10 Hz), 5.71 (1H, br d, J=10 Hz), 6.64 (1H, br d, J=15 Hz), 6.77 (1H, br s), 7.37 (2H, br d, J=8 Hz), 7.40–7.58 (5H, m), 7.64 (1H, br d, J=8 Hz), 7.87 (1H, br t, J=8 Hz), 8.03 (1H, br s), 8.10 (1H, br s), 8.51 (1H, br s), 8.59 (1H, br d, J=8 Hz).

Example 12

8-[2,6-Dichloro-3-[N-methyl-N-[4-(dimethylcarbamoyl)cinnamoylglycyl]amino]benzyloxy]-2-methyl-4-(1,2,4-triazol-1-yl)quinoline was obtained by reacting 8-hydroxy-2-methyl-4-(1,2,4-triazol-1-yl)quinoline with 2,6-dichloro-1-methanesulfonyloxymethyl-3-[N-methyl-N-[4-(dimethylcarbamoy)cinnamoylglycyl]amino]benzene according to a similar manner to that of Example 1-(2).

NMR (CDCl$_3$, δ): 2.82 (3H, s), 2.99 (3H, br s), 3.12 (3H, br s), 3.28 (3H, s), 3.62 (1H, dd, J=17, 4 Hz), 3.93 (1H, dd, J=17, 5 Hz), 5.68 (2H, s), 6.49 (1H, d, J=15 Hz), 6.64 (1H, br t, J=5 Hz), 7.30–7.45 (5H, m), 7.48–7.62 (6H, m), 8.27 (1H, s), 8.57 (1H, s).

its dihydrochloride

NMR (CDCl$_3$—CD$_3$OD, δ): 3.07 (6H, br s), 3.28 (3H, br s), 3.31 (3H, s), 3.90 (1H, br d, J=17 Hz), 4.02 (1H, br d, J=17 Hz), 5.67 (1H, br d, J=10 Hz), 5.50 (1H, d, J=10 Hz), 6.64 (1H, d, J=15 Hz), 7.38 (2H, d, J=8 Hz), 7.46–7.61 (5H, m), 7.71 (1H, d, J=8 Hz), 7.93 (1H, t, J=8 Hz), 8.30–8.42 (3H, m), 9.44 (1H, br s).

Example 13

(1) 3-[N-(Acetylglycyl)-N-methylamino]-1-tert-butyldiphenylsilyloxymethyl-2,6-dichlorobenzene was obtained by reacting 1-tert-butyldiphenylsilyloxymethyl-2,6-dichloro-3-(N-glycyl-N-methylamino)benzene with acetic anhydride according to a similar manner to that of Example 4.

NMR (CDCl$_3$, δ): 1.06 (9H, s), 2.00 (3H, s), 3.21 (3H, s), 3.42 (1H, dd, J=4, 16 Hz), 3.81 (1H, dd, J=5, 16 Hz), 5.88–5.98 (2H, m), 6.40 (1H, br peak), 7.11–7.30 (2H, m), 7.33–7.50 (6H, m), 7.69–7.77 (4H, m).

(2) 3-[N-(Acetylglycyl)-N-methylamino]-2,6-dichloro-1-hydroxymethylbenzene was obtained according to a similar manner to that of Example 11-(2).

NMR (CDCl$_3$, δ): 2.01 (3H, s), 2.18 (1H, t, J=7.5 Hz), 3.23 (3H, s), 3.55 (1H, dd, J=4, 16 Hz), 3.76 (1H, dd, J=5, 16 Hz), 5.00 (2H, d, J=7.5 Hz), 6.41 (1H, br peak), 7.23 (1H, d, J=8 Hz), 7.45 (1H, d, J=8 Hz).

(3) 3-[N-(Acetylglycyl)-N-methylamino]-2,6-dichloro-1-methanesulfonyloxymethylbenzene was obtained according to a similar manner to that of Example 11-(3).

NMR (CDCl$_3$, δ): 2.01 (3H, s), 3.13 (3H, s), 3.24 (3H, s), 3.47 (1H, dd, J=4, 16 Hz), 3.78 (1H, dd, J=5, 16 Hz), 5.53 (2H, s), 6.41 (1H, br peak), 7.35 (1H, d, J=8 Hz), 7.55 (1H, d, J=8 Hz).

(4) 8-[3-[N-(Acetylglycyl)-N-methylamino]-2,6-dichlorobenzyloxy]-2-methyl-4-(pyrazol-1-yl)quinoline was obtained according to a similar manner to that of Example 1-(2).

NMR (CDCl$_3$, δ): 2.00 (3H, s), 2.79 (3H, s), 3.43 (1H, dd, J=4, 16 Hz), 3.79 (1H, dd, J=5, 16 Hz), 5.67 (2H, s), 6.43 (1H, br peak), 6.60 (1H, d, J=2 Hz), 7.23–7.54 (5H, m), 7.77 (1H, d, J=8 Hz), 7.86–7.94 (2H, m).

Example 14

8-[3-[N-(Acetyiglycyl)-N-mnethyiamino]-2,6-dichlorobenzyloxy]-2-methyl-4-(1,2, 4-triazol-1-yl)quinoline was obtained according to a similar manner to that of Example 1-(2).

NMR (CDCl$_3$, δ): 2.01 (3H, s), 2.83 (3H, s), 3.26 (3H, s), 3.47 (1H, dd, J=4, 16 Hz), 3.80 (1H, dd, J=5, 16 Hz), 5.68 (2H, s), 6.42 (1H, br peak), 7.30 (1H, d, J=8 Hz), 7.35–7.42 (2H, m), 7.46–7.63 (3H, m), 8.27 (1H, s), 8.56 (1H, s).

Example 15

8-(2,6-Dichloro-3nitrobenzyloxy)-4-(imidazol-1-yl)-2-methylquinoline was obtained by reacting 8-hydroxy-4-

(imidazol-1-yl)-2-methylquinoline with 2,6-dichloro-1-methanesulfonyloxymethyl-3-nitrobenzene according to a similar manner to that of Example 1-(2).

NMR (CDCl$_3$, δ): 2.80 (3H, s), 5.71 (2H, s), 7.23–7.58 (7H), 7.79 (1H, d, J=48 Hz), 7.84 (1H, d).

Example 16

8-[2,6-Dichloro-3-(N-methylacetamido)benzyloxy]-4-(imidazol-1-yl)-2-methylquinoline dihydrochloride was obtained by reacting 8-hydroxy-4-(imidazol-1-yl)-2-methylquinoline with 2,6-dichloro-3-(N-methylacetamido)benzyl bromide according to a similar manner to that of Example 8.

NMR (DMSO-d$_6$, δ): 1.74 (3H, s), 2.72 (3H, s), 3.10 (3H, s), 5.53 (1H, d, J=12 Hz), 5.58 (1H, d, J=12 Hz), 7.26 (1H, d, J=8 Hz), 7.50–7.80 (4H), 7.86 (1H, s), 8.05 (1H, s), 8.24 (1H, s), 9.68 (1H, s).

Example 17

(1) 8-[2,6-Dichloro-3-[N-(4-ethoxycarbonylcinnamoylglycyl)-N-methylamino]benzyloxy]-4-(imidazol-1-yl)-2-methylquinoline was obtained from 8-[3-(N-glycyl-N-methylamino)-2,6-dichlorobenzyloxy]-4-(imidazol-1-yl)-2-methylquinoline and 4-ethoxycarbonylcinnamic acid according to a similar manner to that of Example 1-(4).

NMR (CDCl$_3$, δ): 1.41 (3H, t, J=7.5 Hz), 2.80 (3H, s), 3.30 (3H, s), 3.68 (1H, dd, J=4, 18 Hz), 3.95 (1H, dd, J=4, 18 Hz), 4.39 (2H, q, J=7.5 Hz), 5.63–5.74 (2H, m), 6.56 (1H, d, J=16 Hz), 6.67 (1H, br peak), 7.23–7.66 (11H, m), 7.85 (1H, s), 8.04 (2H, d, J=8 Hz).

(2) A mixture of 8-[2,6-dichloro-3-[N-(4-ethoxycarbonylcinnamoylglycyl)-N-methylamino]benzyloxy]-4-(imidazol-1-yl)-2-methylquinoline (64 mg), 1N sodium hydroxide solution (0.12 ml) in ethanol was stirred for 4 hours at 60° C. The mixture was concentrated in vacuo, and water was added to the residue. The solution was washed with diethyl ether, and the aqueous layer was adjusted to pH 5 with 1N hydrochloric acid. The resulting precipitate was collected by filtration and washed with water and diethyl ether to give 8-[3-[N-(4-carboxycinnamoylglycyl)-N-methylamino]-2,6-dichlorobenzyloxy]-4-(imidazol-1-yl)-2-methylquinoline (44 mg) as amorphous powder.

NMR (DMSO-d$_6$, δ): 2.67 (3H, s), 3.17 (3H, s), 3.52 (1H, dd, J=5, 16 Hz), 3.82 (1H, dd, J=5, 16 Hz), 5.51 (1H, d, J=10 Hz), 5.59 (1H, d, J=10 Hz), 6.90 (1H, d, J=16 Hz), 7.26–7.35 (2H, m), 7.44 (1H, d, J=16 Hz), 7.49–7.75 (7H, m), 7.80 (1H, s), 7.96 (2H, d, J=8 Hz), 8.21 (1H, s), 8.38 (1H, t-like).

its sodium salt

NMR (DMSO-d$_6$, δ): 2.66 (3H, s), 3.17 (3H, s), 3.51 (1H, dd, J=4, 16 Hz), 3.80 (1H, dd, J=4, 16 Hz), 5.50 (1H, d, J=10 Hz), 5.57 (1H, d, J=10 Hz), 6.76 (1H, d, J=16 Hz), 7.22 (1H, s), 7.27–7.62 (7H, m), 7.68 (1H, s), 7.77–7.86 (4H, m), 8.11 (1H, s), 8.27 (1H, t-like).

Example 18

(1) 8-[2,6-Dichloro-3-[N-(4-ethoxycarbonylcinnamoylglycyl)-N-methylamino]benzyloxy]-2-methyl-4-(morpholino)quinoline was obtained from 8-[3-(N-glycyl-N-methylamino)-2,6-dichlorobenzyloxy]-2-methyl-4-(morpholino)quinoline and 4-ethoxycarbonylcinnamic acid according to a similar manner to that of Example 1-(4).

NMR (CDCl$_3$, δ): 1.40 (3H, t, J=7.5 Hz), 2.69 (3H, s), 3.13–3.23 (4H, m), 3.27 (3H, s), 3.67 (1H, d, J=18 Hz), 3.88–4.02 (5H, m), 4.39 (2H, q, J=7.5 Hz), 5.56–5.70 (2H, m), 6.56 (1H, d, J=16 Hz), 6.70 (1H, br peak), 6.78 (1H, s), 7.19–7.71 (8H, m), 8.04 (2H, d, J=8 Hz).

(2) 8-[3-[N-(4-Carboxycinnamoylglycyl)-N-methylamino]-2,6-dichlorobenzyloxy]-2-methyl-4-(morpholino)quinoline was obtained according to a similar manner to that of Example 17-(2).

NMR (DMSO-d$_6$, δ): 2.53 (3H, s), 3.01–3.21 (7H, m), 3.55 (1H, dd, J=4, 16 Hz), 3.74–3.92 (5H$_1$, m), 5.40–5.56 (2H, m), 6.84–7.03 (2H, m), 7.23–7.73 (7H, m), 7.79 (1H, s), 7.96 (2H, d, J=8 Hz), 8.39 (1H, t-like).

its sodium salt

NMR (DMSO-d$_6$, δ): 2.54 (3H, s), 3.06–3.16 (7H, m), 3.50 (1H, dd, J=4, 16 Hz), 3.71–3.91 (5H, m), 5.44 (1H, d, J=10 Hz), 5.51 (1H, d, J=10 Hz), 6.76 (1H, d, J=16 Hz), 6.93 (1H, s), 7.28 (1H, d, J=8 Hz), 7.31– 7.50 (4H, m), 7.62 (1H, d, J=8 Hz), 7.78 (2H, s-like), 7.84 (2H, d, J=8 Hz), 8.27 (1H, t-like).

Example 19

(1) 1-tert-Butyldiphenylsilyloxymethyl-2,6-dichloro-3-[N-[(E)-3-(6-ethoxycarbonylpyridin-3-yl)acryloylglycyl]-N-methylamino]benzene was obtained from 1-tert-butyldiphenylsilyloxymethyl-2,6-dichloro-3-(N-glycyl-N-methylamino)benzene and (E)-3-(6-ethoxycarbonylpyridin-3-yl)acrylic acid according to a similar manner to that of Example 1-(4).

NMR (CDCl$_3$, δ): 1.06 (9H, s), 1.45 (3H, t, J=7 Hz), 3.23 (3H, s), 3.59 (1H, dd, J=17, 4 Hz), 3.94 (1H, dd, J=17, 5 Hz), 4.49 (2H, q, J=7 Hz), 4.94 (2H, br s), 6.62 (1H, d, J=15 Hz), 6.69 (1H, br s), 7.22 (1H, d, J=8 Hz), 7.34–7.49 (7H, m), 7.60 (1H, d, J=15 Hz), 7.70–7.79 (4H, m), 7.94 (1H, dd, J=8, 2 Hz), 8.14 (1H, d, J=8 Hz), 8.87 (1H, br s).

(2) 2,6-Dichloro-3-[N-[(E)-3-(6-ethoxycarbonylpyridin-3-yl)acryloylglycyl]-N-methylamino]-1-(hydroxymethyl)benzene was obtained according to a similar manner to that of Example 11-(2).

NMR (CDCl$_3$, δ): 1.46 (3H, t, J=7 Hz), 2.27 (1H, br t, J=7 Hz), 3.26 (3H, s), 3.68 (1H, dd, J=17, 4 Hz), 3.90 (1H, dd, J=17, 5 Hz), 4.50 (2H, q, J=7 Hz), 5.02 (2H, br d, J=7 Hz), 6.63 (1H, d, J=15 Hz), 6.74 (1H, br s), 7.28 (1H, d, J=8 Hz), 7.48 (1H, d, J=8 Hz), 7.61 (1H, d, J=15 Hz), 7.94 (1H, dd, J=8, 2 Hz), 8.15 (1H, d, J=8 Hz), 8.85 (1H, br s).

(3) To a stirred solution of 2,6-dichloro-3-[N-[(E)-3-(6-ethoxycarbonylpyridin-3-yl)acryloylglycyl]-N-methylamino]-1-(hydroxymethyl)benzene (150 mg) and triethylamine (60 mg) in N,N-dimethylformamide (1.5 ml) was dropwise added mesyl chloride (35.7 mg) under ice-cooling, and the mixture was stirred for 30 minutes at the same temperature. To the mixture was added 8-hydroxy-4-(imidazol-1-yl)-2-methylquinoline (66.9 mg) and potassium carbonate (205 mg) at ambient temperature, and the mixture was stirred overnight at the same temperature. Water and ethyl acetate were added thereto, and the separated organic layer was washed with 1N sodium hydroxide solution and water, dried over magnesium sulfate and evaporated in vacuo. The residue was purified by flash chromatography on silica gel (chloroform-methanol) to give 8-[2,6-dichloro-3-[N-[(E)-3-(6-ethoxycarbonylpyridin-3-yl)acryloylglycyl]-N-methylamino]benzyloxy]-4-(imidazol-1-yl)-2-methylquinoline (158 mg) as pale yellow amorphous.

NMR (CDCl$_3$, δ): 1.44 (3H, t, J=7.5 Hz), 2.79 (3H, s), 3.28 (3H, s), 3.68 (1H, dd, J=17, 4 Hz), 3.93 (1H, dd, J=17, 5 Hz), 4.48 (2H, q, J=7.5 Hz), 5.64 (1H, d, J=10 Hz), 5.70 (1H, d, J=10 Hz), 6.64 (1H, d, J=15 Hz), 6.74 (1H, br s), 7.29–7.54 (8H, m), 7.60 (1H, d, J=15 Hz), 7.85 (1H, br s), 7.94 (1H, dd, J=8, 2 Hz), 8.13 (1H, d, J=8 Hz), 8.83 (1H, br s).

(4) 8-[3-[N-[(E)-3-(6-Carboxypyridin-3-yl)acryloylglycyl]-N-methylamino]-2,6-dichlorobenzyloxy]-4-(imidazol-1-yl)-2-methylquinoline was obtained according to a similar manner to that of Example 17-(2).

NMR (CDCl$_3$—CD$_3$OD, δ): 2.77 (3H, s), 3.28 (3H, br s), 3.67 (1H, br s), 4.00 (1H, br d, J=17 Hz), 5.63 (2H, br s), 6.73 (1H, br d, J=15 Hz), 7.29–7.60 (9H, m), 7.89–7.98 (2H, m), 8.10 (1H, br s), 8.69 (1H, br s).

its sodium salt

NMR (DMSO-d$_6$, δ): 2.67 (3H, s), 3.16 (3H, s), 3.52 (1H, br dd, J=5, 17 Hz), 3.81 (1H, br dd, J=5, 17 Hz), 5.51 (1H, br d, J=10 Hz), 5.59 (1H, br d, J=10 Hz), 6.88 (1H, d, J=15 Hz), 7.22 (1H, s), 7.30 (1H, d, J=8 Hz), 7.42 (1H, d, J=15 Hz), 7.49–7.59 (4H, m), 7.68 (1H, s), 7.79–7.94 (3H, m), 8.10 (1H, br s), 8.38 (1H, br s), 8.60 (1H, br s).

Example 20

(1) 8-[2,r6-Dichloro-3-[N-[(E)-3-(6-ethoxycarbonylpyridin-3-yl)acryloylglycyl]-N-methylamino]benzyloxy]-2-methyl-4-(morpholino)quinoline was obtained from 8-[3-(N-glycyl-N-methylamino)-2,6-dichlorobenzyloxy]-2-methyl-4-(morpholino)quinoline and (E)-3-(6-ethoxycarbonylpyridin-3-yl)acrylic acid according to a similar manner to that of Example 1-(4).

NMR (CDCl$_3$, δ): 1.45 (1H, t, J=7.5 Hz), 2.66 (3H, s), 3.17–3.25 (4H, m), 3.29 (3H, s), 3.73 (1H, br dd, J=17, 4 Hz), 3.90–4.02 (5H, m), 4.50 (2H, q, J=7.5 Hz), 5.60 (1H, d, J=10 Hz), 5.66 (1H, d, J=10 Hz), 6.67 (1H, d, J=15 Hz), 6.78 (1H, s), 6.83 (1H, br s), 7.20–7.28 (1H, overlapped with CDCl$_3$), 7.31 (1H, d, J=8 Hz), 7.39 (1H, t, J=8 Hz), 7.60 (1H, d, J=15 Hz), 7.68 (1H, br d, J=8 Hz), 7.91 (1H, br d, J=8 Hz), 8.11 (1H, br d, J=8 Hz), 8.73 (1H, br s).

(2) 8-[3-[N-[(E)-3-(6-Carboxypyridin-3-yl)acryloylglycyl]-N-methylamino]-2,6-dichlorobenzyloxy]-2-methyl-4-(morpholino)quinoline was obtained according to a similar manner to that of Example 17-(2).

NMR (CDCl$_3$—CD$_3$OD, δ): 2.67 (3H, br s), 3.25 (3H, s), 3.30–3.45 (4H, m), 3.77 (1H, br d, J=17 Hz), 3.92–4.11 (5H, m), 5.45–5.62 (2H, m), 6.64–7.00 (2H, m), 7.24–7.68 (6H, m), 7.90 (1H, br d, J=8 Hz), 8.04 (1H, br s), 8.70 (1H, br s).

its sodium salt

NMR (DMSO-d$_6$, δ): 2.52 (3H, s), 3.06–3.20 (7H, m), 3.49 (1H, br s), 3.69–3.90 (5H, m), 5.44 (1H, br d, J=10 Hz), 5.50 (1H, br d, J=10 Hz), 6.84–6.98 (2H, m), 7.30 (1H, br d, J=8 Hz), 7.34–7.50 (2H, m), 7.61 (1H, br d, J=8 Hz), 7.73–7.82 (2H, m), 7.91 (1H, s), 8.38 (1H, br s), 8.60 (1H, br s).

Example 21

8-[3-[N-(Acetylglycyl)-N-methylamino]-2,6-dimethylbenzyloxy]-2-methylquinoline was obtained by reacting 8-[3-(N-glycyl-N-methylamino)-2,6-dimethylbenzyloxy]-2-methylquinoline with acetic anhydride according to a similar manner to that of Example 4.

NMR (CDCl$_3$, δ): 2.00 (3H, s), 2.34 (3H, s), 2.51 (3H, s), 2.72 (3H, s), 3.24 (3H, s), 3.49 (1H, dd, J=17, 5 Hz), 3.75 (1H, dd, J=17, 5 Hz), 5.34 (2H, s), 6.48 (1H, br s), 7.03 (1H, d, J=8 Hz), 7.14 (1H, d, J=8 Hz), 7.21–7.31 (2H, m), 7.38–7.47 (2H, m), 8.03 (1H, d, J=8 Hz).

Example 22

8-[3-[N-(Acetylglycyl)-N-methylamino]-2,6-dimethylbenzyloxy]-2,4-dimethylquinoline was obtained by reacting 8-[3-(N-glycyl-N-methylamino)-2,6-dimethylbenzyloxy]-2,4-dimethylquinoline with acetic anhydride according to a similar manner to that of Example 4.

NMR (CDCl$_3$, δ): 2.00 (3H, s), 2.34 (3H, s), 2.51 (3H, s), 2.65 (3H, s), 2.69 (3H, s), 3.23 (3H, s), 3.46 (1H, dd, J=17, 5 Hz), 3.75 (1H, dd, J=17, 5 Hz), 5.33 (2H, s), 6.48 (1H, br s), 7.04 (1H, d, J=8 Hz), 7.11–7.18 (2H, m), 7.23 (1H, d, J=8Hz), 7.45 (1H, t, J=8 Hz), 7.62 (1H, d, J=8 Hz).

What is claimed is:

1. A compound of the formula:

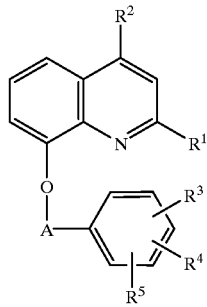

wherein $R^1$ is lower alkyl, $R^2$ is an unsaturated 5- or 6-membered heteromonocyclic group containing 1 to 4 nitrogen atom(s), $R^3$ is hydrogen, lower alkyl or halogen, $R^4$ is lower alkyl or halogen, $R^5$ is nitro or amino substituted with substituent(s) selected from the group consisting of lower alkyl and acyl, and A is lower alkylene, or a pharmaceutically acceptable salt thereof.

2. A compound of claim 1, wherein

A is methylene.

3. A compound of claim 2, wherein $R^5$ is a group of the formula:

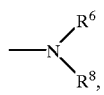

wherein $R^6$ is hydrogen or lower alkyl, $R^8$ is lower alkanoyl or a group of the formula:

or

in which $R^7$ is lower alkanoyl; lower alkylsulfonyl; aroyl; heterocycliccarbonyl; ar(lower)alkenoyl substituted with a substituent selected from the group consisting of lower alkylcarbamoyl, heterocyclic(lower)alkylcarbamoyl, heterocycliccarbamoyl, lower alkanoylamino, heterocyclic(lower)alkanoylamino and heterocycliccarbonylamino; heterocyclic(lower)alkenoyl substituted with a substituent selected from the group consisting of lower alkylcarbamoyl, heterocyclic(lower)alkylcarbamoyl, heterocycliccarbamoyl, lower alkanoylamino, heterocyclic(lower)alkanoylamino and heterocycliccarbonylamino; or arylcarbamoyl substituted with a substituent selected from the group consisting of lower alkylcarbamoyl, heterocyclic(lower) alkylcarbamoyl, heterocycliccarbamoyl, lower alkanoylamino, heterocyclic(lower)alkanoylamino and heterocycliccarbonylamino; and (AA) is amino acid residue.

4. A compound of claim 3, wherein $R^2$ is pyrrolyl, imidazolyl, pyrazolyl, triazolyl or tetrazolyl, $R^5$ is a group of the formula:

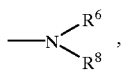

wherein $R^6$ is lower alkyl, $R^8$ is a group of the formula:

in which $R^7$ is lower alkanoyl; lower alkylsulfonyl; benzoyl; pyridylcarbonyl; cinnamoyl substituted with a substituent selected from the group consisting of lower alkylcarbamoyl, pyridyl(lower)alkylcarbamoyl, pyridylcarbamoyl, lower alkanoylamino, pyridyl (lower)alkanoylamino and pyridylcarbonylamino; pyridyl(lower)alkenoyl substituted with a substituent selected from the group consisting of lower alkylcarbamoyl, pyridyl(lower)alkylcarbamoyl, pyridylcarbamoyl, lower alkanoylamino, pyridyl (lower)alkanoylamino and pyridylcarbonylamino; or phenylcarbamoyl substituted with a substituent selected from the group consisting of lower alkylcarbamoyl, pyridyl(lower)alkylcarbamoyl, pyridylcarbamoyl, lower alkanoylamino, pyridyl (lower)alkanoylamino and pyridylcarbonylamino; and (AA) is glycyl.

5. A process for preparing a compound of the formula:

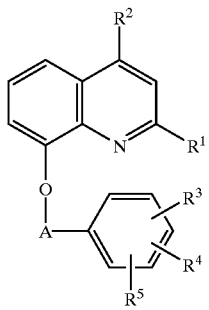

wherein $R^1$ is lower alkyl, $R^2$ is an unsaturated 5- or 6-membered heteromonocyclic group containing 1 to 4 nitrogen atom(s), $R^3$ is hydrogen, lower alkyl or halogen, $R^4$ is lower alkyl or halogen, $R^5$ is nitro or amino substituted with substituent(s) selected from the group consisting of lower alkyl and acyl, and A is lower alkylene, or a salt thereof, which comprises a) reacting a compound of the formula:

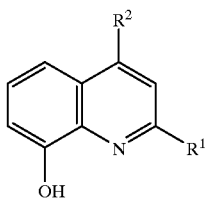

wherein $R^1$ and $R^2$ are each as defined above, or a salt thereof, with a compound of the formula:

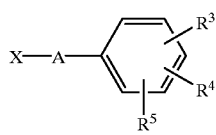

wherein X is a leaving group, and $R^3$, $R^4$, $R^5$ and A are each as defined above, or its salt to give a compound of the formula:

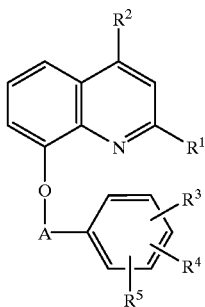

wherein $R^1$, $R^2$, $R^3$, $R^4$, $R^5$ and A are each as defined above, or a salt thereof, or b) acylating a compound of the formula:

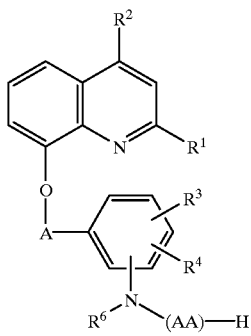

wherein $R^6$ is hydrogen or lower alkyl, (AA) is amino acid residue, and $R^1$, $R^2$, $R^3$, $R^4$ and A are each as defined above, or a salt thereof to give a compound of the formula:

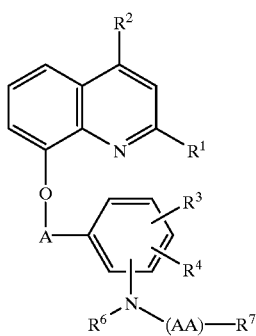

wherein R[7] is acyl, and
R[1], R[2], R[3], R[4], R[6], A and (AA) are each as defined above, or a salt thereof.

6. A pharmaceutical composition comprising a compound of claim 2, as an active ingredient, in association with a pharmaceutically acceptable carrier or excipient.

7. The compound of claim 1, wherein R[2] is selected from the group consisting of pyrrolyl, pyrrolinyl, imidazolyl, pyrazolyl, pyridyl, and its N-oxide, pyrimidinyl, pyrazinyl, pyridazinyl, triazolyl, tetrazolyl, and dihydrotriazinyl.

8. A method of treating a disease mediated by bradykinin, comprising administering an effective amount of the compound of claim 1 to a human being or an animal in need thereof.

9. A method of treating a disease mediated by bradykinin, comprising administering an effective amount of the compound of claim 1 to a human being in need thereof.

10. A method of treating a disease mediate by bradykinin selected from the group consisting of allergy, inflammation, autoimmune disease, shock and pain, comprising administering an effective amount of the compound of claim 1 to a human being or an animal in need thereof.

11. A method of treating a disease mediated by bradykinin selected from the group consisting of allergy, inflammation, autoimmune disease, shock and pain, comprising administering an effective amount of the compound of claim 1 to a human being thereof.

12. A pharmaceutical composition, comprising the compound of claim 1 and a pharmaceutically acceptable carrier or diluent.

* * * * *

UNITED STATES PATENT AND TRADEMARK OFFICE
CERTIFICATE OF CORRECTION

PATENT NO. : 6,083,959

DATED : July 4, 2000

INVENTOR(S): Teruo OKU, et al.

It is certified that an error appears in the above-identified patent and that said Letters Patent is hereby corrected as shown below:

On the Title Page, Item [87] the PCT Publication Number and Date are incorrect. They should read as follows:

[87] PCT Pub. No.: WO/97/41104
     PCT Pub. Date: Nov. 6, 1997

Signed and Sealed this

Seventeenth Day of April, 2001

Attest:

NICHOLAS P. GODICI

Attesting Officer      Acting Director of the United States Patent and Trademark Office